(12) United States Patent
Liu et al.

(10) Patent No.: US 8,771,995 B2
(45) Date of Patent: Jul. 8, 2014

(54) ENZYMATIC SYNTHESIS OF SULFATED POLYSACCHARIDES

(75) Inventors: Jian Liu, Chapel Hill, NC (US); Robert J. Linhardt, Albany, NY (US); Fikri Y. Avci, Boston, MA (US); Ava M. Munoz, Santiago de Compostela (ES); Jinghua Chen, Wuhan (CN)

(73) Assignees: The University of North Carolina at Chapel Hill, Chapel Hill, NC (US); Rensselaer Polytechnic Institute, Troy, NY (US)

( * ) Notice: Subject to any disclaimer, the term of this patent is extended or adjusted under 35 U.S.C. 154(b) by 0 days.

(21) Appl. No.: 13/417,641

(22) Filed: Mar. 12, 2012

(65) Prior Publication Data

US 2012/0322114 A1 Dec. 20, 2012

Related U.S. Application Data

(63) Continuation of application No. 11/920,319, filed as application No. PCT/US2006/018778 on May 12, 2006, now abandoned.

(60) Provisional application No. 60/680,392, filed on May 12, 2005.

(51) Int. Cl.
*C12P 19/04* (2006.01)
*C12N 9/10* (2006.01)
*C07H 21/04* (2006.01)
*C07K 1/00* (2006.01)

(52) U.S. Cl.
USPC ........... 435/101; 435/193; 536/23.2; 530/350

(58) Field of Classification Search
USPC .................. 435/101, 193; 536/23.2; 530/350
See application file for complete search history.

(56) References Cited

U.S. PATENT DOCUMENTS

| | | | |
|---|---|---|---|
| 5,817,487 A | 10/1998 | Kobayashi et al. | |
| 5,834,282 A | 11/1998 | Habuchi et al. | |
| 5,935,824 A | 8/1999 | Sgarlato | |
| 6,255,088 B1 * | 7/2001 | Wong et al. | 435/130 |
| 6,861,254 B1 * | 3/2005 | Rosenberg et al. | 435/325 |
| 2004/0191870 A1 | 9/2004 | Rosenberg et al. | |
| 2005/0255562 A1 | 11/2005 | Rosenberg et al. | |

FOREIGN PATENT DOCUMENTS

| WO | WO 2004/005475 | | 1/2004 |
|---|---|---|---|
| WO | WO 2004/017910 | * | 3/2004 |

OTHER PUBLICATIONS

Habuchi et al., The occurrence of three isoforms of heparan sulfate 6-O-sulfotransferase having different specificities for hexuronic acid adjacent to the trageted N-sulfoglucosamine. J.. Biol. Chem., 2000, vol. 275: 2859-2868.*
Broun et al., "Catalytic plasticity of fatty acid modification enzymes underlying chemical diversity of plant lipids," Science, 1998, 282:1315-1317.
Chen et al., "Enzymatic redesigning of biologically active haparan sulfate," JBC, 2004, 280(52):42817-42825.
Chica et al., "Semi-rational approaches to engineering enzyme activity: combining the benefits of directed evolution and rational design," Curr. Opin. Biotechnol., 2005, 16:378-384.
Devos et al., "Practical Limits on Function Prediction," Proteins: Structure, Function and Genetics, 2000, 41:98-107.
Kisselev et al., "Polypeptide release factors in prokaryotes and eukaryotes: same function, different structure," Structure, 2002, 10:8-9.
Sen et al., "Developments in directed evolution for improving enzyme functions,"Appl. Biochem. Biotechnol., 2007, 143:212-223.
Wishart et al., "A single mutation converts a novel phosphotyrosine binding domain into a dual-specificity phosphatase," J. Biol. Chem., 1995, 270(45):26782-26785.
Burkart et al., "Regeneration of PAPS for the Enzymatic Synthesis of sulfated Oligosaccharides," J. Org. Chem., 2000, 65:5565-5574.
Saribas et al., "Production of N-sulfated polysaccharides using yeast-expressed N-deacetylase/N-sulfotransferase-1 (NDST-1)," Glycobiology, 2004, 14(12):1217-1228.

* cited by examiner

*Primary Examiner* — Ganapathirama Raghu
(74) *Attorney, Agent, or Firm* — Foley & Lardner LLP

(57) ABSTRACT

Heparin is synthesized from a polysaccharide comprised of a 1-4 glycosidically linked alternating polymer of uronic acid and glucosamine residues, wherein the uronic acid is selected from iduronic and glucuronic acid, wherein the glucosamine is partially N-sulfated; by a series of selective reactions catalyzed by recombinant enzymes.

6 Claims, 4 Drawing Sheets

ENZYMATIC SYNTHESIS OF SULFATED POLYSACCHARIDES

RELATED APPLICATIONS

This application is a continuation of U.S. application Ser. No. 11/920,319 filed Dec. 9, 2008, now abandoned, which is the U.S. national stage of PCT/US2006/018778, filed May 12, 2006, and published in English on Nov. 23, 2006 as WO 2006/124801; and claims the benefit of U.S. Provisional Patent Application Ser. No. 60/680,392, filed May 12, 2005; the disclosure of which is incorporated herein by reference in its entirety.

GOVERNMENT INTEREST

The presently disclosed subject matter was made with U.S. Government support under Grant No. AI50050 awarded by the National Institutes of Health. Thus, the U.S. Government has certain rights in the presently disclosed subject matter.

TECHNICAL FIELD

The presently disclosed subject matter relates generally to methods of sulfating polysaccharides. In particular, the presently disclosed subject matter relates to methods of sulfating polysaccharides using O-sulfotransferases, which includes a reaction condition that reduces potential inhibitory effects from sulfur donor byproducts.

BACKGROUND

Heparan sulfate (HS) is a ubiquitous component of the cell surface and extracellular matrix. It regulates a wide range of physiologic and pathophysiologic functions, including embryonic development and blood coagulation, and can facilitate viral infection (Esko and Selleck (2002) *Annu. Rev. Biochem.* 71, 435-471; Liu and Thorp (2002) *Med. Res. Rev.* 22, 1-25). HS exerts its biological effects by interacting with the specific proteins involved in a given process (Capila and Lindhardt (2002) *Angew. Chem. Int. Ed.* 41, 390-412). HS is a highly charged polysaccharide consisting of 1→4-linked glucosamine and glucuronic/iduronic acid units that contain both N- and O-sulfo groups. Unique saccharide sequences within HS determine the specificity of the binding of HS to its target proteins (Linhardt (2003) *J. Med. Chem.* 46, 2551-2564). Heparin, a specialized form of HS, is a commonly used anticoagulant drug. Thus, new methods for the synthesis of heparin and HS attract considerable interest for those developing anticoagulant and other HS-related drugs having improved pharmacological effects.

Chemical synthesis has been the major route to obtain structurally defined heparin and HS oligosaccharides (Petitou and van Boeckel (2004) *Angew. Chem. Int. Ed.* 43, 3118-3133). One example of a chemically synthesized HS oligosaccharide is a synthetic pentasaccharide having anti-thrombin-binding properties marketed in the United States under the trade name ARIXTRA® (GlaxoSmithKline, Middlesex, United Kingdom). ARIXTRA® is a specific factor Xa inhibitor that is used clinically to prevent venous thromboembolic incidents during surgery.

Unfortunately, the total synthesis of heparin and HS oligosaccharides, larger than pentasaccharides, is difficult. HS analogues with 14 saccharide units inhibit the activity of thrombin, but these synthetic analogues are simplified hybrid molecules of HS oligosaccharides and highly sulfated glucose units (Petitou et al. (1999) *Nature* 398, 417-422; Dementiev et al. (2004) *Nat. Struct. Biol.* 11, 867-863) and are not the naturally occurring structures. Although the pursuit for the chemical synthesis of heparin and HS oligosaccharides (Avci et al. (2003) *Curr. Pharm. Des.* 9, 2323-2335) continues, it has become clear that chemical synthesis alone is currently incapable of generating most larger oligosaccharide structures. Thus, the application of HS biosynthetic enzymes for generating large heparin and HS oligosaccharides with desired biological activities offers a promising alternative approach.

Six classes of enzymes are involved in HS biosynthesis. HS is initially synthesized as a copolymer of D-glucuronic acid and N-acetylglucosamine (GlcNAc) through the action of D-glucuronyl and N-acetyl-D-glucosaminyltransferase (Lindahl et al. (1998) *J. Biol. Chem.* 273, 24979-24982). Next, a series of modifications take place, including N-deacetylation and N-sulfation (carried out by N-deacetylase/N-sulfotransferase) of the glucosamine residue to form N-sulfoglucosamine (GlcNS), $C_5$ epimerization of glucuronic acid (carried out by epimerase) to form L-iduronic acid (IdoUA), 2-O-sulfation of IdoUA (carried out by 2-O-sulfotransferase (2-OST)), 6-O-sulfation of glucosamine (carried out by 6-O-sulfotransferase (6-OST)), and 3-O-sulfation of glucosamine (carried out by 3-O-sulfotransferase (3-OST)) (Sasisekharan et al. (2002) *Nat. Rev. Cancer* 2, 521-528). The reactions catalyzed by 2-OST, 6-OST, and 3-OST are shown in FIG. 1A.

Enzymes "in the pathway" for HS biosynthesis have been cloned and expressed, and have been employed in the synthesis of HS polysaccharides. Kuberan and Rosenberg (Balagurunathan et al. (2003) *Nat. Biotechnol.* 21, 1343-1346; Kuberan et al. (2003) *J. Am. Chem. Soc.* 125, 12424-12425; Balagurunathan et al. (2003) *J. Biol. Chem.* 278, 52613-52621) utilized these enzymes to synthesize an HS containing antithrombin binding sites with anticoagulant activity. Although this approach demonstrated for the first time the feasibility of enzymatic synthesis of HS, only about 1 µg of product was generated, making extensive structural characterization and biological studies impossible. Recently, Lindahl and colleagues reported an alternative chemoenzymatic approach for the synthesis of anticoagulant heparin from heparosan, the *E. coli* K5 capsular polysaccharide (Lindahl et al. (2005) *J. Med. Chem.* 48, 349-352). This method utilized the $C_5$ epimerase to convert D-glucuronic acid to IdoUA, followed by the chemical persulfation and finally selective desulfation. Although this approach afforded approximately 5 g of a heparin-like polysaccharide with anticoagulant activity, unnatural saccharide units, such as 3-O-sulfo-D-glucuronic acid, were present in their product. This suggested a limitation in the selectivity of chemical sulfation/desulfation in HS synthesis. Further, the OST catalyzed sulfation reaction utilizes 3'-phosphoadenosine 5'-phosphosulfate (PAPS) as the sulfur donor, producing adenosine 3',5'-diphosphate (PAP). PAP can compete with PAPS for OST binding, which can result in inhibition of the sulfation reaction over time as PAP concentration increases in the reaction mixture.

Thus, developing an effective and highly selective approach for O-sulfation of polysaccharides remains an unmet need in the art for the large scale synthesis of HS.

SUMMARY

This Summary lists several embodiments of the presently disclosed subject matter, and in many cases lists variations and permutations of these embodiments. This Summary is merely exemplary of the numerous and varied embodiments.

Mention of one or more representative features of a given embodiment is likewise exemplary. Such an embodiment can typically exist with or without the feature(s) mentioned; likewise, those features can be applied to other embodiments of the presently disclosed subject matter, whether listed in this Summary or not. To avoid excessive repetition, this Summary does not list or suggest all possible combinations of such features.

In some embodiments of the presently disclosed subject matter, a method of sulfating a polysaccharide is provided, comprising (a) providing a reaction mixture comprising at least one O-sulfotransferase (OST) enzyme and 3'-phosphoadenosine 5'-phosphosulfate (PAPS); (b) incubating a polysaccharide substrate with the reaction mixture, wherein production of the sulfated polysaccharide from the polysaccharide substrate is catalyzed by the OST enzyme with a conversion of the PAPS to adenosine 3',5'-diphosphate (PAP); and (c) providing a reaction condition which modifies PAP to reduce an inhibitory effect of PAP on the polysaccharide sulfation. In some embodiments, providing the reaction condition comprises providing a PAPS regeneration system comprising a PAPS regenerating enzyme and a sulfur donor compound, wherein the PAPS regenerating enzyme catalyzes regeneration of the PAPS from the PAP utilizing the sulfur donor compound as a substrate. In some embodiments, the PAPS regenerating enzyme is an arylsulfotransferase, such as for example AST-IV. In some embodiments, the sulfur donor compound is an aryl sulfate compound, such as for example p-nitrophenol sulfate (PNPS). In some embodiments, providing the reaction condition comprises providing a phosphatase enzyme, wherein the phosphatase enzyme modifies the PAP.

In some embodiments of the presently disclosed subject matter, a method of sulfating a polysaccharide is provided, comprising (a) providing a reaction mixture comprising PAP, a PAPS regenerating enzyme and a sulfur donor compound; (b) incubating the reaction mixture for a time period sufficient to catalyze the production of PAPS from the PAP by the PAPS regenerating enzyme utilizing the sulfur donor compound as a substrate, such as for example a time period from about 1 minute to about 30 minutes; and (c) incubating a polysaccharide substrate and at least one OST enzyme with the reaction mixture, wherein production of a sulfated polysaccharide from the polysaccharide substrate is catalyzed by the OST enzyme with a conversion of the PAPS to PAP and wherein the PAPS regenerating enzyme catalyzes regeneration of the PAPS from the PAP utilizing the sulfur donor compound as a substrate. In some embodiments, the PAPS regenerating enzyme is an arylsulfotransferase, such as for example AST-IV. In some embodiments, the donor compound is an aryl sulfate compound, such as for example PNPS.

In some embodiments of the methods for sulfating polysaccharides, the at least one OST enzyme is selected from the group consisting of 2-OST, 3-OST-1, 3-OST-3, 6-OST, and combinations thereof. In some embodiments, the at least one OST enzyme is a recombinant OST enzyme, which is, in some embodiments, produced in a bacterial expression system. Further, in some embodiments, the OST enzyme is a fusion protein, such as for example a maltose-binding protein (MBP)-2-OST fusion protein or a MBP-6-OST fusion protein. In some embodiments, the OST enzyme is immobilized on a substrate, such as for example an agarose bead.

In some embodiments of the methods for sulfating polysaccharides, the polysaccharide substrate is a chemically desulfated N-sulfated (CDSNS) heparin. In some embodiments, the polysaccharide substrate is partially sulfated prior to reaction mixture incubation. In some embodiments, the sulfated polysaccharide is a glycosaminoglycan (GAG), such as for example a heparan sulfate (HS). In some embodiments, the sulfated polysaccharide is an HS that is an anticoagulant-active HS, an antithrombin-binding HS, a fibroblast growth factor (FGF)-binding HS, a herpes simplex virus envelope glycoprotein D-binding HS, or has a combination of these properties.

In some embodiments of the presently disclosed subject matter, a kit for sulfating a polysaccharide is provided. In some embodiments, the kit comprises at least one OST enzyme and a reagent which modifies PAP to reduce an inhibitory effect of PAP on polysaccharide sulfation. In some embodiments, the kit further comprising instructions for sulfating a polysaccharide. In some embodiments, the at least one OST enzyme is contained within a first container and the reagent is contained within a second container. In some embodiments, the at least one OST enzyme is selected from the group consisting of 2-OST, 3-OST-1, 3-OST-3, 6-OST, and combinations thereof. Further, in some embodiments, the OST enzyme is a recombinant OST enzyme, such as for example a recombinant OST enzyme produced in a bacterial expression system. In some embodiments, the OST enzyme is a fusion protein, such as for example a maltose-binding protein (MBP)-2-OST fusion protein or a MBP-6-OST fusion protein. In some embodiments, the OST enzyme is immobilized on a substrate, such as for example an agarose bead.

In some embodiments of the kit, the reagent comprises a PAPS regeneration system comprising a PAPS regenerating enzyme (e.g., an arylsulfotransferase, such as AST-IV) and a sulfur donor compound (e.g., an aryl sulfate compound, such as PNPS. In other embodiments of the kit, the reagent comprises a phosphatase enzyme.

Accordingly, it is an object of the presently disclosed subject matter to provide for the enzymatic synthesis of sulfated polysaccharides. This object is achieved in whole or in part by the presently disclosed subject matter.

An object of the presently disclosed subject matter having been stated above, other objects and advantages will become apparent to those of ordinary skill in the art after a study of the following description of the presently disclosed subject matter and non-limiting examples.

BRIEF DESCRIPTION OF THE DRAWINGS

FIG. 1A shows the stepwise enzymatic synthesis of sulfated polysaccharides using HS O-sulfotransferases. The description of intermediate polysaccharides is disclosed in the Examples herein below. Compounds 4a and 4b were prepared by inverting the order of sulfation steps. 4a was prepared by incubating compound 1 with 2-OST followed by 6-OST, whereas 4b was prepared by incubating compound 1 with 6-OST followed by 2-OST. FIG. 1B shows the reaction catalyzed by arylsulfotransferase IV (AST-IV) to generate PAPS. R represents —H or —SO$_3$.

FIGS. 3A-3E show the chromatograms of the disaccharide analysis of compounds 1, 2, 3, 4a, and 4b, from FIG. 1A respectively. The numbers above peaks indicate the eluted positions of authentic disaccharide standards, where 1 represents ΔUA-GlcNAc, 2 represents ΔUA-GlcNS, 3 represents ΔUA-GlcNS6S, 4 represents ΔUA2S-GlcNS, and 5 represents ΔUA2S-GlcNS6S. * marks the eluted position of Δ UA2S-GlcNAc. The quantity of ΔUA2S-GlcNAc not determined.

FIG. 4A, BaF3 FGFR1c cells were seeded in 96-well plates as described with 2 nM FGF2 for control and 2 nM FG F2 plus a 1 µg/ml concentration of the following compounds: heparin, 1, 2, 3, 4a, and 4b (FIG. 1A). FIG. 4B shows dose-response curves of heparin, 4a, and 4b for their activities in stimulating cell proliferation. Cells were cultured for 40 hours (h), followed by incubating in the media containing [$^3$H]thymidine for 4 h. The cellular proliferation was determined by [$^3$H]thymidine incorporation into the DNA. heparin (●); 4a (○); and 4b (▼). Data are mean±range of duplicates.

DETAILED DESCRIPTION

Figure 1:
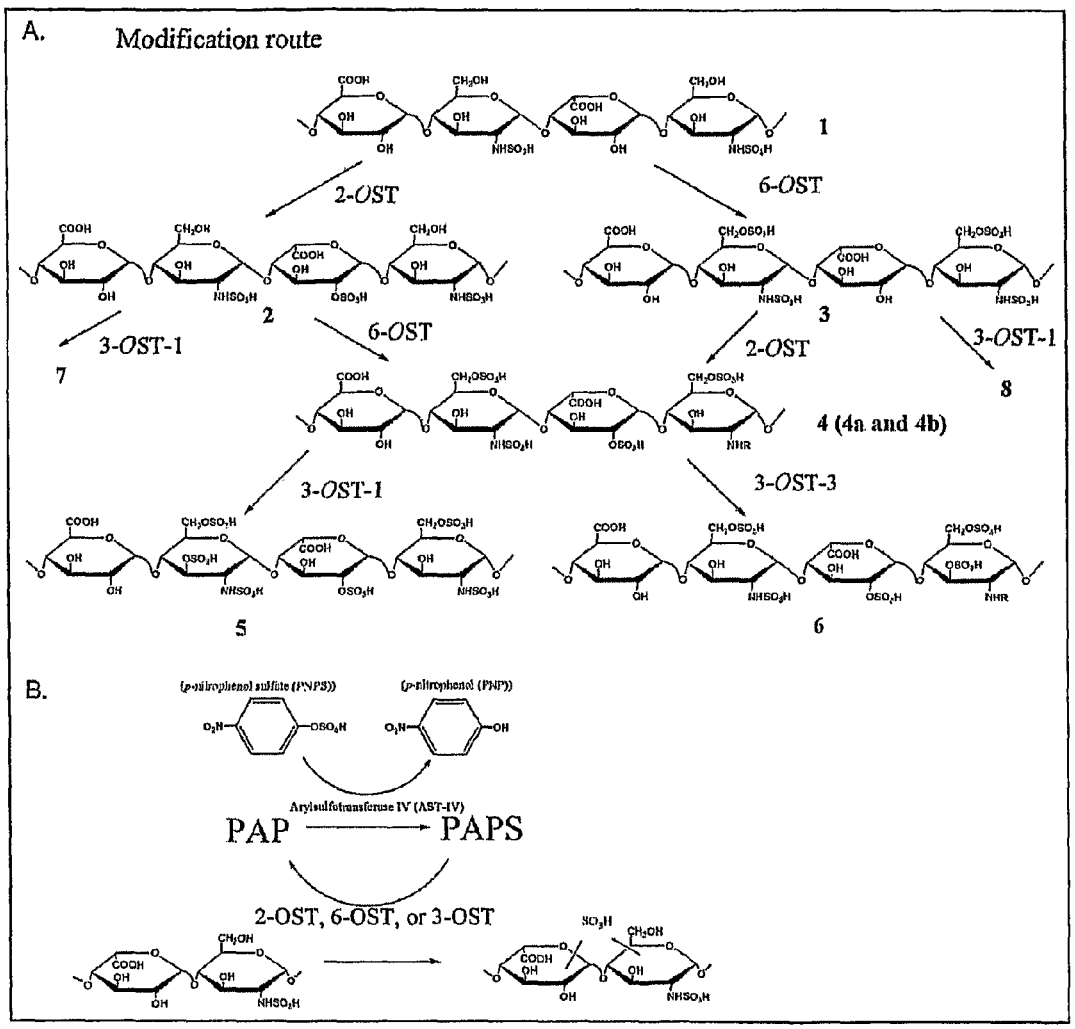
FIGS. 1A and 1B are schematic drawings showing synthesis of sulfated polysaccharides coupled with a PAPS enzymatic regeneration system.

The details of one or more embodiments of the presently disclosed subject matter are set forth in the accompanying description below. Other features, objects, and advantages of the presently disclosed subject matter will be apparent from the detailed description, and from the claims. All publications, patent applications, patents, and other references mentioned herein are incorporated by reference in their entirety. Some of the polynucleotide and polypeptide sequences disclosed herein are cross-referenced to GENBANK® accession numbers. The sequences cross-referenced in the GENBANK® database are expressly incorporated by reference as are equivalent and related sequences present in GENBANK® or other public databases. Also expressly incorporated herein by reference are all annotations present in the GENBANK® database associated with the sequences disclosed herein. In case of conflict, the present specification, including definitions, will control.

I. General Considerations

Heparan sulfates (HSs) are highly sulfated polysaccharides, present on the surface of mammalian cells and in the extracellular matrix in large quantities. HS is a highly charged polysaccharide consisting of 1→4-linked glucosamine and glucuronic/iduronic acid units that contain both N- and O-sulfo groups. Heparin, a specialized form of HS, is a commonly used anticoagulant drug. Thus, "heparan sulfate", as used herein, includes heparin.

HSs play critical roles in a variety of important biological processes, including assisting viral infection, regulating blood coagulation and embryonic development, suppressing tumor growth, and controlling the eating behavior of test subjects by interacting with specific regulatory proteins (Liu, J., and Thorp, S. C. (2002) *Med. Res. Rev.* 22:1-25; Rosenberg, R. D., et al., (1997) *J. Clin. Invest.* 99:2062-2070; Bernfield, M., et al., (1999) *Annu. Rev. Biochem.* 68:729-777; Alexander, C. M., et al., (2000) *Nat. Genet.* 25:329-332; Reizes, O., et al., (2001) *Cell* 106:105-116). The unique sequences determine to which specific proteins HSs bind, thereby regulating biological processes.

The biosynthesis of HS occurs in the Golgi apparatus. It is initially synthesized as a copolymer of glucuronic acid and N-acetylated glucosamine by D-glucuronyl and N-acetyl-D-glucosaminyltransferase, followed by various modifications (Lindahl, U., et al., (1998) *J. Biol. Chem.* 273:24979-24982). These modifications include N-deacetylation and N-sulfation of glucosamine, $C_5$ epimerization of glucuronic acid to form iduronic acid residues, 2-O-sulfation of iduronic and glucuronic acid, as well as 6-O-sulfation and 3-O-sulfation of glucosamine. Several enzymes that are responsible for the biosynthesis of HS have been cloned and characterized (Esko, J. D., and Lindahl, U. (2001) *J. Clin. Invest.* 108:169-173).

The expression levels of various HS biosynthetic enzyme isoforms contribute to the synthesis of specific saccharide sequences in specific tissues. HS N-deacetylase/N-sulfotransferase, 3-O-sulfotransferase, and 6-O-sulfotransferase are present in multiple isoforms. Each isoform is believed to recognize a saccharide sequence around the modification site in order to generate a specific sulfated saccharide sequence (Liu, J., et al., (1999) *J. Biol. Chem.* 274:5185-5192; Aikawa, J.-I., et al., (2001) *J. Biol. Chem.* 276:5876-5882; Habuchi, H., et al., (2000) *J. Biol. Chem.* 275:2859-2868). For instance, HS D-glucosaminyl 3-O-sulfotransferase (3-OST) isoforms generate 3-O-sulfated glucosamine residues that are linked to different sulfated uronic acid residues. 3-OST isoform 1 (3-OST-1) transfers sulfate to the 3-OH position of an N-sulfated glucosamine residue that is linked to a glucuronic acid residue at the nonreducing end (GlcUA-GlcNS±6S). However, 3-OST isoform 3 (3-OST-3) transfers sulfate to the 3-OH position of an N-unsubstituted glucosamine residue that is linked to a 2-O-sulfated iduronic acid at the nonreducing end (IdoUA2S-GlcNH$_2$±6S) (Liu, J., et al., (1999) *J. Biol. Chem.* 274:38155-38162). The difference in the substrate specificity of 3-OSTs results in distinct biological functions. For example, the HS modified by 3-OST-1 binds to antithrombin (AT) and possesses anticoagulant activity (Liu, J., et al., (1996) *J. Biol. Chem.* 271:27072-27082). However, the HS modified by 3-OST-3 (3-OST-3A and 3-OST-3B) binds to glycoprotein D (gD) of herpes simplex virus, type 1, (HSV-1) thus mediating viral entry (Shukla, D., et al., (1999) *Cell* 99:13-22).

The HS- and heparin-regulated anticoagulation mechanisms have been studied extensively. It is now known that HS, including heparin, interact with AT, a serine protease inhibitor, to inhibit the activities of thrombin and factor Xa in the blood coagulation cascade (Rosenberg, R. D., et al., (1997) *J. Clin. Invest.* 99:2062-2070). Anticoagulant-active HS (HS$^{act}$) and heparin contain one or multiple AT-binding sites per polysaccharide chain. This binding site contains a specific pentasaccharide sequence with a structure of -GlcNS (or Ac)6S-GlcUA-GlcNS3S(±6S)-IdoUA2S-GlcNS6S-. The 3-O-sulfation of glucosamine for generating GlcNS3S(±6S) residue, which is carried out by 3-OST-1, is an important modification for the synthesis of HS$^{act}$ (Liu, J., et al., (1996) *J. Biol. Chem.* 271:27072-27082; Shworak, N. W., et al., (1997) *J. Biol. Chem.* 272:28008-28019).

Cell surface HS also assists HSV-1 infection (WuDunn, D., and Spear, P. G. (1989) *J. Virol.* 63:52-58). One report (Shukla, D., et al., (1999) *Cell* 99:13-22) suggests that a specific 3-O-sulfated HS is involved in assisting HSV-1 entry. The 3-O-sulfated HS is generated by 3-OST-3 but not by 3-OST-1. In addition, the 3-O-sulfated HS provides binding sites for HSV-1 envelope glycoprotein D, which is a key viral protein involved in the entry of HSV-1 (Shukla, D., et al., (1999) *Cell* 99:13-22). Because 3-OST-3-modified HS is rarely found in HS from natural sources, the study suggests that HSV-1 recognizes a unique saccharide structure. Indeed, the result from the structural characterization of a gD-binding octasaccharide revealed that the octasaccharide possesses a specific saccharide sequence (Liu, J., et al., (2002) *J. Biol. Chem.* 277:33456-33467). In addition, the binding affinity of the 3-O-sulfated HS for gD is about 2 µM (Shukla, D., et al., *Cell* 99:13-22). This affinity is similar to that reported for the binding of gD to the protein receptors, suggesting that HSV-1 utilizes both protein and HS cell surface receptors to infect target cells (Willis, S. H., et al., (1998) *J. Virol.* 72:5938-5947; Krummenacher, C., et al., (1999) *J. Virol.* 73:8127-8137). It is believed that the interaction between gD and the 3-O-sulfated HS or the protein entry receptors somehow triggers the fusion between the virus and the cell in the presence of other viral envelope proteins, including gB, gH, and gL (Shukla, D., and Spear, P. G. (2001) *J. Clin. Invest.* 108:503-510). A study of the co-crystal structure of gD and herpes entry receptor HveA suggests that the binding of HveA to gD induces conformational changes in gD (Carfi, A., et al., (2001) *Mol. Cell* 8:169-179).

II. Methods of Sulfating Polysaccharides

The presently disclosed subject matter provides enzymatic methods for the sulfation of multimilligram amounts of heparan sulfate having particular functions using sulfotransferases coupled with a system for reducing inhibitory effects from sulfur donor byproducts. In some embodiments, the system for reducing inhibitory byproducts comprises a 3'-phosphoadenosine 5'-phosphosulfate regeneration system. In other embodiments, the system comprises a phosphatase enzyme. By utilizing the presently disclosed sulfation system and selecting appropriate enzymatic modification steps, an inactive precursor polysaccharide can been converted to a heparan sulfate having desired biological properties.

In some embodiments, the presently disclosed subject matter employs recombinant sulfotransferases. Because the recombinant sulfotransferases can be recombinantly expressed in bacteria, and the disclosed methods can use low cost sulfo donors, the presently disclosed subject matter can be readily utilized to synthesize large quantities of biologically active heparan sulfates while reducing the production of reaction inhibitory byproducts.

Two advantages provided by the presently disclosed subject matter facilitate the large scale synthesis of HS. First, large amounts of all the required HS sulfotransferases can be successfully recombinantly expressed in *Escherichia coli*. Second, the enzymatic sulfation reactions are coupled with a system for reducing inhibitory effects from sulfur donor byproducts (e.g., PAP) and reducing costs related to continuously providing a supply of the sulfur donor PAPS. PAPS, a universal sulfate donor and source of sulfate for all sulfotransferases, is a highly expensive and unstable molecule that has been an obstacle to the large-scale production of enzymatically sulfated products. The half-life of PAPS in aqueous solution at pH 8.0 is approximately 20 hours. Product inhibition by adenosine 3',5'-diphosphate (PAP) has also been a limiting factor to large-scale applications. For example, PAP inhibition of hydroxysteroid sulfotransferase was determined to be $K_i=14$ µM (Marcus et al. (1980) *Aial. Biochem.* 107, 296). PAP has also been shown to inhibit the sulfotransferase NodST with a $K_i=0.1$ µM (Lin et al., (1995) *J. Am. Chem. Soc.* 117, 8031). In some embodiments of the presently disclosed subject matter, a PAPS regeneration system, such as the system developed by Burkhart and colleagues (Burkhart et al. (2000) *J. Org. Chem.* 65, 5565-5574, incorporated herein by reference), has been modified and adapted to be coupled to the enzymatic synthesis reactions. The PAPS regeneration system converts PAP into PAPS, thereby reducing accumulation of inhibitory PAP in the reaction mixture and reducing production costs related to providing PAPS to drive the sulfation reaction. In other embodiments, phosphatase enzymes can be utilized to modify PAP so that it no longer has binding affinity for sulfotransferases.

The presently disclosed sulfation system can be adapted to produce a multitude of HS molecules having varied biological activities by selecting appropriate sulfotransferases to include and by sequentially controlling the addition of those sulfotransferases to the reaction system to facilitate appropriate timing of sulfations of the polysaccharide template. For example, as disclosed herein, HS having specific biological activities can be synthesized utilizing the presently disclosed methods, including anticoagulant HS, fibroblast growth factor-2-binding activity, herpes simplex virus glycoprotein D (gD)-binding HS, and fibroblast growth factor 2 (FGF2) receptor-binding HS. Only two or three enzymatic steps are required for the synthesis of each of these biologically-active HS molecules (FIG. 1A). Thus, the presently disclosed subject matter provides an efficient and effective method for the large scale synthesis of a wide range of HS with specific activity required. In addition, this method provides a model system to better understand the biosynthesis of HS.

In some embodiments of the presently disclosed subject matter, a method of sulfating a polysaccharide is provided. In some embodiments, the method comprises incubating a polysaccharide substrate to be sulfated with a reaction mixture that comprises at least one sulfotransferase enzyme, such as for example an O-sulfotransferase (OST) enzyme, and a sulfur donor, such as for example PAPS. Production of the sulfated polysaccharide from the polysaccharide substrate is catalyzed by the OST enzyme with a conversion of the PAPS to adenosine 3',5'-diphosphate (PAP). A reaction condition is further provided that modifies generated PAP to reduce an inhibitory effect of PAP on the polysaccharide sulfation. For example, a PAPS regeneration system can be occupied wan the sulfation reaction to convert PAP into PAPS or phosphatases can be added to the reaction mixture to modify PAP such that it does not compete with PAPS for binding with OSTs.

In some embodiments, the polysaccharide substrate is a previously N,O-desulfated and re-N-sulfated polysaccharide, such as for example a chemically desulfated N-sulfated (CDSNS) heparin. In other embodiments, the polysaccharide substrate is partially sulfated prior to reaction mixture incubation. For example, a CDSNS can be reacted with a particular OST to produce a sulfated polysaccharide intermediate product that can then be reacted with a different OST to further sulfate the polysaccharide at different locations. This sequential process of reacting the polysaccharide substrate with different OSTs can be continued until a final polysaccharide is produced exhibiting desired biological activities (based, at least in part, on the sulfation pattern of the polysaccharide). FIG. 1A schematically illustrates several exemplary polysaccharide substrates sequentially reacted with different OSTs to produce different intermediate and end products. For example, compound 1 can be reacted with 2-OST and then 6-OST to produce compound 4a or compound 1 can be reacted with 6-OST and then 2-OST to produce compound 4b, each having fibroblast growth factor (FGF)-binding activity. Further, compounds 4a or 4b can be reacted with 3-OST-1 to produce compound 5 having antithrombin-binding and anticoagulant activities. Alternatively, compounds 4a or 4b can be reacted with 3-OST-3 to produce compound 6 having herpes simplex virus (HSV) envelope glycoprotein D (gD) binding activity. As such, the presently disclosed subject matter provides for the production of HS compounds having different biological properties based on the selection and sequential reaction of different OSTs with polysaccharide substrates. The polysaccharide substrate can be reacted with different OST enzymes by addition of each enzyme sequentially to the same reaction mixture, or intermediate polysaccharide products can be purified from the reaction mixture after reaction of a particular OST and then reacted with a different OST. In some embodiments, depending on the desired final product, different OST enzymes can be added to the reaction mixture simultaneously.

In some embodiments the sulfated polysaccharide product can be a glycosaminoglycan (GAG). GAGs are the most abundant heteropolysaccharides in the body. These molecules are long unbranched polysaccharides containing a repeating disaccharide unit. The disaccharide units can contain either of two modified sugars: N-acetylgalactosamine (GalNAc) or N-acetylglucosamine (GlcNAc) and a uronic acid such as glucuronate or iduronate. GAGs are highly negatively charged molecules, with extended conformation that imparts high viscosity to the solution. Along with the high viscosity of GAGs comes low compressibility, which makes these molecules ideal for a lubricating fluid in the joints. At the same time, their rigidity provides structural integrity to cells and provides passageways between cells, allowing for cell migration. The specific GAGs of physiological significance are hyaluronic acid, dermatan sulfate, chondroitin sulfate, heparin, heparan sulfate (including heparin), and keratan sulfate. Thus, in some embodiments, the sulfated polysaccharide product is a HS. In some embodiments, the sulfated polysaccharide product is an anticoagulant-active HS, an antithrombin-binding HS, an FGF-binding HS, and an HSV gD-binding HS.

II.A. Sulfotransferases

As previously noted, the presently disclosed subject matter utilizes sulfotransferases, particularly O-sulfotransferases (OSTs), to sulfate polysaccharides. Sulfotransferases comprise a family of enzymes that catalyze the transfer of a sulfonate or sulfuryl group ($SO_3$) from the cofactor 3'-phosphoadenosine-5'-phosphosulfate (PAPS) to an acceptor molecule. Even though it is more accurate to call these sulfonation reactions, the term sulfation is still widely used. Therefore, the term "sulfation" as used herein refers to a transfer of a sulfonate or sulfuryl group from one molecule to another.

Sulfotransferases mediate sulfation of different classes of substrates such as carbohydrates, oligosaccharides, peptides, proteins, flavonoids, and steroids for a variety of biological functions including signaling and modulation of receptor binding (Bowman et al., (1999) Chem. Biol. 6, R9-R22; and Falany (1997) FASEB J. 11, 1-2). Within the past few years, many new sulfotransferases have been identified and cloned (Aikawa et al., (1999) J. Biol. Chem. 274, 2690; Dooley (1998) Chemico-Biol. Interact. 109, 29; Fukuta et al. (1998) Biochim. Biophys. Act. 1399, 57; Habuchi et al., (1998) J. Biol. Chem. 273, 9208; Mazany et al., (1998) Biochim. Biophys. Act. 1407, 92; Nastuk et al. (1998) J. Neuroscience 18, 7167; Ong et al., (1998) J. Biol. Chem. 273, 5190; Ouyang et al., (1998) J. Biol. Chem. 273, 24770; Saeki et al. (1998) J. Biochem. 124, 55; Uchimura et al. (1998) J. Biol. Chem. 273, 22577; and Yoshinari et al., (1998) J. Biochem. 123, 740).

As used herein, the term "O-sulfotransferase (OST)" includes polypeptides and nucleic acids encoding HS O-sulfotransferases, such as for example "2-OST" (e.g., mouse 2-OST, GENBANK® Accession No. AAC40135 (SEQ ID NO:1); "3-OST-1" (e.g., human 3-OST-1, GENBANK® Accession No. NP_005105 (SEQ ID NO:2); "3-OST-3" (e.g., human 3-OST-3A, GENBANK® Accession No. NP_006033 (SEQ ID NO:3) and human 3-OST-3B, GENBANK® Accession No. NP_006032 (SEQ ID NO:4); and "6-OST" (e.g., mouse 6-OST-1, GENBANK® Accession No. NP_056633 (SEQ ID NO:5), mouse 6-OST-2, GENBANK® Accession No. BAA89247 (SEQ ID NO:6), and mouse 6-OST-3, GENBANK® Accession No. NP_056635 (SEQ ID NO:7)), which are HS 2-O-sulfotransferase, HS 3-O-sulfotransferase isoform 1, HS 3-O-sulfotransferase isoform 3, and HS 6-O-sulfotransferase, respectively.

The term "OST" includes invertebrate and vertebrate homologs of the O-sulfotransferases (e.g., mammalian (such as human and mouse), insect, and avian homologs). As such, although exemplary embodiments of particular OSTs have been disclosed herein, the presently disclosed subject matter is not intended to be limited to the disclosed examples, but rather "OST", including particular OSTs (e.g., 2-OST, 3-OST-1, 3-OST-3, and 6-OST), includes all comparable OSTs known to the skilled artisan.

The terms "OST gene product", "OST protein", and "OST polypeptide" refer to peptides having amino acid sequences which are substantially identical to native amino acid sequences from the organism of interest and which are biologically active in that they comprise all or a part of the amino acid sequence of a HS O-sulfotransferase isoform, or cross-react with antibodies raised against a HS O-sulfotransferase isoform polypeptide, or retain all or some of the biological activity of the native amino acid sequence or protein. Such biological activity can include immunogenicity.

The terms "OST gene product", "OST protein", and "OST polypeptide" also include analogs of HS O-sulfotransferase molecules. By "analog" is intended that a DNA or peptide sequence can contain alterations relative to the sequences disclosed herein, yet retain all or some of the biological activity of those sequences. Analogs can be derived from genomic nucleotide sequences as are disclosed herein or from other organisms, or can be created synthetically. Those skilled in the art will appreciate that other analogs, as yet undisclosed or undiscovered, can be used to design and/or construct OST analogs. There is no need for a "OST gene product", "OST protein", and "OST polypeptide" to comprise all or substantially all of the amino acid sequence of a native OST gene product. Shorter or longer sequences are anticipated to be of use in the presently disclosed subject matter, shorter sequences are herein referred to as "segments." Thus, the terms "OST gene product", "OST protein", and "OST polypeptide" also include fusion or recombinant HS O-sulfotransferase polypeptides and proteins comprising sequences of the OST protein. Methods of preparing such proteins are known in the art. For example, in some embodiments, the OST is a 2-OST or a 6-OST fusion protein, such as a maltose-binding protein (MBP)-2-OST fusion protein or a MBP-6-OST fusion protein, as disclosed herein.

The terms "OST gene", "OST gene sequence", and "OST gene segment" refer to any DNA sequence that is substantially identical to a polynucleotide sequence encoding a HS O-sulfotransferase isoform gene product, protein or polypeptide as defined above, and can also comprise any combination of associated control sequences. The terms also refer to RNA, or antisense sequences, complementary to such DNA sequences. As used herein, the term "DNA segment" refers to a DNA molecule that has been isolated free of total genomic DNA of a particular species. Furthermore, a DNA segment encoding a HS O-sulfotransferase polypeptide refers to a DNA segment that contains OST coding sequences, yet is isolated away from, or purified free from, total genomic DNA of a source species, such as for example Homo sapiens. Included within the term "DNA segment" are DNA segments and smaller fragments of such segments, and also recombinant vectors, including, for example, plasmids, cosmids, phages, viruses, and the like.

The term "substantially identical", when used to define either a OST gene product or amino acid sequence, or a OST gene or nucleic acid sequence, means that a particular sequence varies from the sequence of a natural OST by one or more deletions, substitutions, or additions, the net effect of which is to retain at least some of biological activity of the natural gene, gene product, or sequence. Such sequences include "mutant" sequences, or sequences in which the biological activity is altered to some degree but retains at least some of the original biological activity.

Alternatively, DNA analog sequences are "substantially identical" to specific DNA sequences disclosed herein if: (a) the DNA analog sequence is derived from coding regions of the natural OST gene; or (b) the DNA analog sequence is capable of hybridization of DNA sequences of (a) under stringent conditions and which encode biologically active OST gene products; or (c) the DNA sequences are degenerate as a result of alternative genetic code to the DNA analog sequences defined in (a) and/or (b). Substantially identical analog proteins will be greater than about 60%, 70%, 80%, 90%, 95%, 96%, 97%, 98%, or 99% identical to the corresponding sequence of the native protein. Sequences having lesser degrees of identity but comparable biological activity are considered to be equivalents. In determining nucleic acid sequences, all subject nucleic acid sequences capable of encoding substantially similar amino acid sequences are considered to be substantially similar to a reference nucleic acid sequence, regardless of differences in codon sequences or substitution of equivalent amino acids to create biologically functional equivalents.

Sequence identity or percent similarity of a DNA or peptide sequence can be determined, for example, by comparing sequence information using the GAP computer program, available from the University of Wisconsin Geneticist Computer Group. The GAP program utilizes the alignment method of Needleman et al. (1970) *J Mol Biol* 48:443, as revised by Smith et al. (1981) *Adv Appl Math* 2:482. Briefly, the GAP program defines similarity as the number of aligned symbols (i.e., nucleotides or amino acids) that are similar, divided by the total number of symbols in the shorter of the two sequences. The preferred parameters for the GAP program are the default parameters, which do not impose a penalty for end gaps. See Schwartz et al. (1979) *Nuc Acids Res* 6(2):745-755; Gribskov et al. (1986) *Nuc Acids Res* 14(1):327-334.

In certain embodiments, the present subject matter concerns the use of OST genes and gene products that include within their respective sequences a sequence that is essentially that of an OST gene, or the corresponding protein. The term "a sequence essentially as that of an OST gene", means that the sequence is substantially identical or substantially similar to a portion of an OST gene and contains a minority of bases or amino acids (whether DNA or protein) which are not identical to those of an OST protein or an OST gene, or which are not a biologically functional equivalent. The term "biologically functional equivalent" is well understood in the art and is further defined in detail herein. Nucleotide sequences are "essentially the same" where they have between about 75% and about 85% or more preferably, between about 86% and about 90%, or more preferably greater than 90%, or more preferably between about 91% and about 95%, or even more preferably, between about 96% and about 99%; of nucleic acid residues which are identical to the nucleotide sequence of a OST gene. Similarly, peptide sequences which have about 60%, 70%, 80%, or 90%, or preferably from 90-95%, or more preferably greater than 96%, or more preferably 95-98%, or most preferably 96%, 97%, 98%, or 99% amino acids which are identical or functionally equivalent or biologically functionally equivalent to the amino acids of an OST polypeptide will be sequences which are "essentially the same".

OST gene products and OST encoding nucleic acid sequences, which have functionally equivalent codons, are also covered by the presently disclosed subject matter. The term "functionally equivalent codon" is used herein to refer to codons that encode the same amino acid, such as the ACG and AGU codons for serine. Applicants contemplate substitution of functionally equivalent codons of Table 1 into sequences of OSTs disclosed herein as equivalents.

TABLE 1

Functionally Equivalent Codons

| Amino Acids | | | Codons |
|---|---|---|---|
| Alanine | Ala | A | GCA GCC GCG GCU |
| Cysteine | Cys | C | UGC UGU |
| Aspartic Acid | Asp | D | GAC GAU |
| Glutamic acid | Glu | E | GAA GAG |
| Phenylalanine | Phe | F | UUC UUU |
| Glycine | Gly | G | GGA GGC GGG GGU |
| Histidine | His | H | CAC CAU |
| Isoleucine | Ile | I | AUA AUC AUU |
| Lysine | Lys | K | AAA AAG |
| Leucine | Leu | L | UUA UUG CUA CUC CUG CUU |
| Methionine | Met | M | AUG |
| Asparagine | Asn | N | AAC AAU |
| Proline | Pro | P | CCA CCC CCG CCU |
| Glutamine | Gln | Q | CAA CAG |
| Arginine | Arg | R | AGA AGG CGA CGC CGG CGU |
| Serine | Ser | S | ACG AGU UCA UCC UCG UCU |
| Threonine | Thr | T | ACA ACC ACG ACU |
| Valine | Val | V | GUA GUC GUG GUU |
| Tryptophan | Trp | W | UGG |
| Tyrosine | Tyr | Y | UAC UAU |

It will also be understood by those of skill in the art that amino acid and nucleic acid sequences can include additional residues, such as additional N- or C-terminal amino acids or 5' or 3' nucleic acid sequences, and yet still be encompassed by the OSTs disclosed herein, so long as the sequence retains biological protein activity where protein expression is concerned. The addition of terminal sequences particularly applies to nucleic acid sequences which can, for example, include various non-coding sequences flanking either of the 5' or 3' portions of the coding region or can include various internal sequences, i.e., introns, which are known to occur within genes.

The present subject matter also encompasses the use of nucleotide segments that are complementary to the sequences of the present subject matter, in one embodiment, segments that are fully complementary, i.e. complementary for their entire length. Nucleic acid sequences that are "complementary" are those, which are base-paired according to the standard Watson-Crick complementarity rules. As used herein, the term "complementary sequences" means nucleic acid sequences which are substantially complementary, as can be assessed by the same nucleotide comparison set forth above, or is defined as being capable of hybridizing to the nucleic acid segment in question under relatively stringent conditions such as those described herein. A particular example of a complementary nucleic acid segment is an antisense oligonucleotide.

One technique in the art for assessing complementary sequences and/or isolating complementary nucleotide sequences is hybridization. Nucleic acid hybridization will be affected by such conditions as salt concentration, temperature, or organic solvents, in addition to the base composition, length of the complementary strands, and the number of nucleotide base mismatches between the hybridizing nucleic acids, as will be readily appreciated by those skilled in the art. Stringent temperature conditions will generally include temperatures in excess of about 30° C., typically in excess of about 37° C., and preferably in excess of about 45° C. Stringent salt conditions will ordinarily be less than about 1,000 mM, typically less than about 500 mM, and preferably less than about 200 mM. However, the combination of parameters is much more important than the measure of any single parameter. See e.g., Wethmur & Davidson (1968) *J Mol Biol* 31:349-370. Determining appropriate hybridization conditions to identify and/or isolate sequences containing high levels of homology is well known in the art. See e.g., Sambrook et al. (2001) *Molecular Cloning: A Laboratory Manual*, Third Edition, Cold Spring Harbor Laboratory Press, Cold Spring Harbor, N.Y.

For the purposes of specifying conditions of high stringency, preferred conditions are salt concentration of about 200 mM and temperature of about 45° C. One example of such stringent conditions is hybridization at 4×SSC, at 65° C., followed by a washing in 0.1×SSC at 65° C. for one hour. Another exemplary stringent hybridization scheme uses 50% formamide, 4×SSC at 42° C. Another example of "stringent conditions" refers to conditions of high stringency, for example 6×SSC, 0.2% polyvinylpyrrolidone, 0.2% Ficoll, 0.2% bovine serum albumin, 0.1% sodium dodecyl sulfate, 100 µg/ml salmon sperm DNA and 15% formamide at 68° C. Nucleic acids having sequence similarity are detected by hybridization under low stringency conditions, for example, at 50° C. and 10×SSC (0.9 M NaCl/0.09 M sodium citrate) and remain bound when subjected to washing at 55° C. in 1×SSC. Sequence identity can be determined by hybridization under stringent conditions, for example, at 50° C. or higher and 0.1×SSC (9 mM NaCl/0.9 mM sodium citrate).

Nucleic acids that are substantially identical to the provided OSTs, e.g., allelic variants, genetically altered versions of the gene, etc., bind to the disclosed OSTs under stringent hybridization conditions. By using probes, particularly labeled probes of DNA sequences, one can isolate homologous or related genes. The source of homologous genes can be any species, e.g., primate species, particularly human; rodents, such as rats and mice; canines; felines; bovines; ovines; equines; insects; yeasts; nematodes; etc.

Between mammalian species, e.g., human, mouse and rat, homologs have substantial sequence similarity, i.e. at least 75% sequence identity between nucleotide sequences. Sequence similarity is calculated based on a reference sequence, which can be a subset of a larger sequence, such as a conserved motif, coding region, flanking region, etc. A reference sequence will usually be at least about 18 nucleotides long, more usually at least about 30 nucleotides long, and can extend to the complete sequence that is being compared. Algorithms for sequence analysis are known in the art, such as BLAST, described in Altschul et al. (1990) *J Mol Biol* 215:403-410. The sequences provided herein are essential for recognizing OST related and homologous proteins in database searches.

At a biological level, identity is just that, i.e. the same amino acid at the same relative position in a given family member of a gene family. Homology and similarity are generally viewed as broader terms. For example, biochemically similar amino acids, for example leucine and isoleucine or glutamate/aspartate, can be present at the same position—these are not identical per se, but are biochemically "similar". As disclosed herein, these are referred to as conservative differences or conservative substitutions. This differs from a conservative mutation at the DNA level, which changes the nucleotide sequence without making a change in the encoded amino acid, e.g., TCC to TCA, both of which encode serine.

When percentages are referred to herein, it is meant to refer to percent identity. The percent identities referenced herein can be generated by alignments with the program GENEWORKS™ (Oxford Molecular, Inc. of Campbell, Calif., U.S.A.) and/or the BLAST program at the NCBI website. Another commonly used alignment program is entitled CLUSTAL W and is described in Thompson et al. (1994) *Nucleic Acids Res* 22(22):4673-4680, among other places.

The term "gene" is used for simplicity to refer to a functional protein, polypeptide or peptide encoding unit. As will be understood by those in the art, this functional term includes both genomic sequences and cDNA sequences.

As noted above, modifications and changes can be made in the structure of the OST proteins and peptides described herein and still constitute a molecule having like or otherwise desirable characteristics. For example, certain amino acids can be substituted for other amino acids in a protein structure without appreciable loss of interactive capacity with, for example, structures in the nucleus of a cell. Since it is the interactive capacity and nature of a protein that defines that protein's biological functional activity, certain amino acid sequence substitutions can be made in a protein sequence (or the nucleic acid sequence encoding it) to obtain a protein with the same, enhanced, or antagonistic properties. Such properties can be achieved by interaction with the normal targets of the native protein, but this need not be the case, and the biological activity of the presently disclosed subject matter is not limited to a particular mechanism of action. It is thus contemplated in accordance with the present subject matter that various changes can be made in the sequence of the OST proteins and peptides or underlying nucleic acid sequence without appreciable loss of their biological utility or activity.

Biologically functional equivalent peptides, as used herein, are peptides in which certain, but not most or all, of the amino acids can be substituted. Thus, applicants contemplate substitution of codons that encode biologically equivalent amino acids as described herein into the sequences of the disclosed OSTs, but which are not set forth herein in their entirety for convenience.

Alternatively, functionally equivalent proteins or peptides can be created via the application of recombinant DNA technology, in which changes in the protein structure can be engineered, based on considerations of the properties of the amino acids being exchanged. Changes designed by man can be introduced through the application of site-directed mutagenesis techniques, e.g., to introduce improvements to the antigenicity of the protein or to test OST mutants in order to examine OST sulfotransferase activity, or other activity at the molecular level.

Amino acid substitutions, such as those which might be employed in modifying the OST proteins and peptides described herein, are generally based on the relative similarity of the amino acid side-chain substituents, for example, their hydrophobicity, hydrophilicity, charge, size, and the like. An analysis of the size, shape and type of the amino acid side-chain substituents reveals that arginine, lysine and histidine are all positively charged residues; that alanine, glycine and serine are all of similar size; and that phenylalanine, tryptophan and tyrosine all have a generally similar shape. Therefore, based upon these considerations, arginine, lysine and histidine; alanine, glycine and serine; and phenylalanine, tryptophan and tyrosine; are defined herein as biologically functional equivalents. Other biologically functionally equivalent changes will be appreciated by those of skill in the art.

In making biologically functional equivalent amino acid substitutions, the hydropathic index of amino acids can be considered. Each amino acid has been assigned a hydropathic index on the basis of their hydrophobicity and charge characteristics, these are: isoleucine (+4.5); valine (+4.2); leucine (+3.8); phenylalanine (+2.8); cysteine (+2.5); methionine (+1.9); alanine (+1.8); glycine (−0.4); threonine (−0.7); serine (−0.8); tryptophan (−0.9); tyrosine (−1.3); proline (−1.6); histidine (−3.2); glutamate (−3.5); glutamine (−3.5); aspartate (−3.5); asparagine (−3.5); lysine (−3.9); and arginine (−4.5).

The importance of the hydropathic amino acid index in conferring interactive biological function on a protein is generally understood in the art (Kyte et al. (1982) *J Mol Biol* 157:105, incorporated herein by reference). It is known that certain amino acids can be substituted for other amino acids having a similar hydropathic index or score and still retain a similar biological activity. In making changes based upon the hydropathic index, the substitution of amino acids whose hydropathic indices are within ±2 of the original value is preferred, those, which are within ±1 of the original value, are particularly preferred, and those within ±0.5 of the original value are even more particularly preferred.

It is also understood in the art that the substitution of like amino acids can be made effectively on the basis of hydrophilicity. U.S. Pat. No. 4,554,101, incorporated herein by reference, states that the greatest local average hydrophilicity of a protein, as governed by the hydrophilicity of its adjacent amino acids, correlates with its immunogenicity and antigenicity, i.e. with a biological property of the protein. It is understood that an amino acid can be substituted for another having a similar hydrophilicity value and still obtain a biologically equivalent protein.

As detailed in U.S. Pat. No. 4,554,101, the following hydrophilicity values have been assigned to amino acid residues: arginine (+3.0); lysine (+3.0); aspartate (+3.0±1); glutamate (+3.0±1); serine (+0.3); asparagine (+0.2); glutamine (+0.2); glycine (0); threonine (−0.4); proline (−0.5±1); alanine (−0.5); histidine (−0.5); cysteine (−1.0); methionine (−1.3); valine (−1.5); leucine (−1.8); isoleucine (−1.8); tyrosine (−2.3); phenylalanine (−2.5); tryptophan (−3.4).

In making changes based upon similar hydrophilicity values, the substitution of amino acids whose hydrophilicity values are within ±2 of the original value is preferred, those, which are within ±1 of the original value, are particularly preferred, and those within ±0.5 of the original value are even more particularly preferred.

While discussion has focused on functionally equivalent polypeptides arising from amino acid changes, it will be appreciated that these changes can be effected by alteration of the encoding DNA, taking into consideration also that the genetic code is degenerate and that two or more codons can code for the same amino acid.

Thus, it will also be understood that the presently disclosed subject matter is not limited to the particular nucleic acid and amino acid sequences of the OSTs disclosed herein. Recombinant vectors and isolated DNA segments can therefore variously include the O-sulfotransferase polypeptide-encoding region itself, include coding regions bearing selected alterations or modifications in the basic coding region, or include larger polypeptides which nevertheless comprise the O-sulfotransferase polypeptide-encoding regions or can encode biologically functional equivalent proteins or peptides which have variant amino acid sequences. Biological activity of an O-sulfotransferase can be determined using techniques generally known in the art, for example as disclosed herein in the Examples.

The nucleic acid segments of the present subject matter, regardless of the length of the coding sequence itself, can be combined with other DNA sequences, such as promoters, enhancers, polyadenylation signals, additional restriction enzyme sites, multiple cloning sites, other coding segments, and the like, such that their overall length can vary considerably. It is therefore contemplated that a nucleic acid fragment of almost any length can be employed, with the total length preferably being limited by the ease of preparation and use in the intended recombinant DNA protocol. For example, nucleic acid fragments can be prepared which include a short stretch complementary to a nucleic acid sequence set forth in any of the OSTs disclosed herein, such as about 10 nucleotides, and which are up to 10,000 or 5,000 base pairs in length, with segments of 3,000 being preferred in certain cases. DNA segments with total lengths of about 4,000, 3,000, 2,000, 1,000, 500, 200, 100, and about 50 base pairs in length are also contemplated to be useful.

Recombinant vectors form further aspects of the present subject matter. Particularly useful vectors are those in which the coding portion of the DNA segment is positioned under the control of a promoter. The promoter can be that naturally associated with the OST gene, as can be obtained by isolating the 5' non-coding sequences located upstream of the coding segment or exon, for example, using recombinant cloning and/or polymerase chain reaction (PCR) technology and/or other methods known in the art, in conjunction with the compositions disclosed herein.

In other embodiments, it is contemplated that certain advantages will be gained by positioning the coding DNA segment under the control of a recombinant, or heterologous, promoter. As used herein, a recombinant or heterologous promoter is a promoter that is not normally associated with a 3-O-sulfotransferase gene in its natural environment. Such promoters can include promoters isolated from bacterial, viral, eukaryotic, or mammalian cells. Naturally, it will be important to employ a promoter that effectively directs the expression of the DNA segment in the cell type chosen for expression. The use of promoter and cell type combinations for protein expression is generally known to those of skill in the art of molecular biology (See, e.g., Sambrook et al. (2001) *Molecular Cloning: A Laboratory Manual*, Third Edition, Cold Spring Harbor Laboratory Press, Cold Spring Harbor, N.Y.). The promoters employed can be constitutive or inducible and can be used under the appropriate conditions to direct high level expression of the introduced DNA segment, such as is advantageous in the large-scale production of recombinant proteins or peptides.

In some embodiments of the method disclosed herein for sulfating polysaccharides, the OST enzyme is immobilized on a substrate. This provides an advantage in that the substrate to which the OSTs are attached can be washed after a sulfation reaction to remove all components of the reaction except the bound OSTs. As such, the products of the reaction can be more easily separated from the enzymes catalyzing the reaction and the OSTs can be recycled and utilized again in multiple sulfation reactions. In some embodiments, the substrate is agarose. In particular embodiments, the agarose substrate is an agarose bead and the OSTs are linked to the beads.

II.B. Reduction of Inhibitory Effects of PAP

The presently disclosed method for sulfating polysaccharides can comprise providing a "reaction condition" that modifies PAP to reduce inhibitory effects of PAP, such as competing with PAPS for binding with OSTs, on the polysaccharide sulfation. In some embodiments, the reaction condition comprises a phosphatase enzyme. The phosphatase enzyme can remove a phosphate from the PAP, which reduces its binding affinity for OSTs. In some embodiments, the phosphatase is 3'-ribonucleotide phosphohydrolase.

In some embodiments, the reaction condition is a PAPS regeneration system, which comprises a PAPS regenerating enzyme and a sulfur donor compound. The PAPS regenerating enzyme catalyzes regeneration of the PAPS from the PAP utilizing the sulfur donor compound as a substrate. See, e.g., U.S. Pat. No. 6,255,088; Burkart et al., (2000) *J. Org. Chem.* 65, 5565-5574, which is herein incorporated by reference in its entirety. Thus, the PAPS regeneration system provides the dual advantages of reducing the inhibitory effects of PAP accumulation on sulfotransferase activity while also constantly "recharging" the reaction mixture with the primary sulfur donor molecule, PAPS.

Thus, an aspect of the presently disclosed subject matter is directed to a sulfur donor compound (e.g., PAPS) regeneration process coupled with sulfation of a polysaccharide substrate. In particular, the process can be of a type wherein the sulfation of a polysaccharide substrate is catalyzed by a sulfotransferase, such as one or more OSTs, with a conversion of 3'-phosphoadenosine-5'-phosphosulfate (PAPS) to adenosine 3',5'-diphosphate (PAP). The sulfation process can be coupled with an enzymatic regeneration of the 3'-phosphoadenosine-5'-phosphosulfate from the adenosine 3',5'-diphosphate. The enzymatic regeneration can employ an arylsulfotransferase as the catalyst and an aryl sulfate as a substrate. As previously disclosed, preferred carbohydrate substrates can include GAGs, such as for example heparan sulfates, including heparin.

In some embodiments, the arylsulfotransferase is a recombinant aryl sulfotransferase IV (AST-IV; e.g., rat AST-IV (SEQ ID NO:8)). This enzyme, when coupled to a sulfotransferase of choice, transfers sulfate from an aryl sulfate (e.g., p-nitrophenyl sulfate (PNPS) to PAP. This system averts product inhibition by PAP while regenerating PAPS in situ and can be monitored quantitatively by measurement of the absorbance of released p-nitrophenol at 400 nm.

The enzyme AST-IV exists in two oxidative forms (Marshall et al., (1997) *J. Biol. Chem.* 272, 9153-9160; Marshall et al., (1998) *Chem. -Biol. Interact.* 109, 107-116; Yang et al., (1998) *Chem. -Biol. Interact.* 109, 129-135; Yang et al. (1996) *Protein Expression Purif.* 8, 423-429; Guo et al. (1994) *Chem. -Biol. Interact.* 92, 25-31; Chen et al. (1992) *Protein Expression Purif.* 3, 421-6; Lin et al. (1998) *Anal. Biochem.* 264, 111-117; and Yang et al., (1997) *Protein Eng.* 10, 70). These two oxidative forms can be easily resolved (Yang et al. (1996) *Protein Expression Purif.* 8, 423-429), and the resolved physiologically relevant form has been utilized to assay picomole quantities of PAPS and PAP (Lin et al. (1998) *Anal. Biochem.* 264, 111-117). As the bacterial expression of rat AST-IV has been demonstrated (Chen et al., (1992) *Protein Expression Purif.* 3, 421-6; and Ozawa et al., (1990) *Nucleic Acids Res.* 18, 4001z.), AST IV can be cloned from a rat liver cDNA library, overexpressed in a recombinant bacterial system (e.g., *E. coli*) and isolated (See, e.g., U.S. Pat. No. 6,255,088, herein incorporated by reference in its entirety).

Coupling the sulfotransferase catalyzed sulfation reaction with a PAPS regeneration system can provide a further advantage of generating PAPS utilized in the reaction directly from PAP. That is, the reaction mixture can be formulated to combine PAP with a PAPS regenerating enzyme prior to or simultaneously with addition of a sulfotransferase to the reaction mixture. The PAPS regenerating enzyme can then generate PAPS from the PAP for use by the sulfotransferase, thereby alleviating the need of supplying any of the more expensive and unstable PAPS to the reaction mixture. As such, in some embodiments of the presently disclosed subject matter a method of sulfating a polysaccharide is provided comprising providing a reaction mixture comprising therein adenosine 3',5'-diphosphate (PAP), a PAPS regenerating enzyme and a sulfur donor compound (other than PAPS) and incubating the reaction mixture for a time period sufficient to catalyze the production of 3'-phosphoadenosine 5'-phosphosulfate (PAPS) from the PAP by the PAPS regenerating enzyme utilizing the sulfur donor compound as a substrate. The method further comprises incubating a polysaccharide substrate and at least one O-sulfotransferase (OST) enzyme with the reaction mixture, wherein production of a sulfated polysaccharide from the polysaccharide substrate is catalyzed by the OST enzyme with a conversion of the PAPS to PAP and wherein the PAPS regenerating enzyme then catalyzes regeneration of the PAPS from the PAP, again utilizing the sulfur donor compound as a substrate.

III. Kits

The presently disclosed subject matter further provides kits for sulfating polysaccharides. In some embodiments, the kit comprises at least one sulfotransferase enzyme (e.g., at least one OST); and a reagent which modifies adenosine 3',5'-diphosphate (PAP) to reduce an inhibitory effect of PAP on the polysaccharide sulfation. In some embodiments of the kit the at least one sulfotransferase enzyme is contained within a first container and the reagent is contained within a second container. The kit can further comprise instructions for sulfating a polysaccharide.

In some embodiments of the kit, the at least one sulfotransferase enzyme is an OST enzyme selected from the group consisting of 2-OST, 3-OST-1, 3-OST-3, 6-OST, and combinations thereof. In some embodiments, the OST enzyme is a recombinant OST enzyme, such as for example a recombinant OST enzyme produced in a bacterial expression system. In some embodiments, the OST enzyme is a fusion protein, such as for example a MBP-2-OST fusion protein or a MBP-6-OST fusion protein. Further, in some embodiments, the OST enzyme is immobilized to a substrate, such as for example an agarose bead.

In some embodiments of the kit, the reagent comprises a PAPS regeneration system comprising a PAPS regenerating enzyme (e.g., AST-IV) and a sulfur donor compound (e.g., PNPS). In other embodiments of the kit, the reagent comprises a phosphatase enzyme (e.g., 3'-ribonucleotide phosphohydrolase).

EXAMPLES

The following Examples provide illustrative embodiments. In light of the present disclosure and the general level of skill in the art, those of skill will appreciate that the following Examples are intended to be exemplary only and that numerous changes, modifications, and alterations can be employed without departing from the scope of the presently claimed subject matter.

Materials and Methods for Examples 1-3

Preparation of Chemically Desulfated N-Sulfated Heparin (CDSNS Heparin). Treatment of heparin with a dimethyl sulfoxide/methanol mixture (9:1, v/v) at 80° C. for 24 h resulted in nearly complete N,O-desulfation with <5% of the solvolytically resistant O-sulfo groups remaining. Chemical N-sulfation with sulfur trioxide-pyridine afforded CDSNS heparin, which was characterized by disaccharide analysis and $^1$H and two-dimensional COSY NMR.

Expression and Purification of 2-OST and 6-OST. The catalytic domains of 2-OST of Chinese hamster ovary ($Arg^{51}$-$Asn^{356}$) and mouse 6-OST-1 ($His^{53}$-$Trp^{401}$) were cloned into a pMAL-c2X vector (New England Biolabs, Beverly, Mass., U.S.A.) using the BamHI and HindIII sites to generate maltose-binding protein (MBP)-2-OST and MBP-6-OST fusion proteins. The full-length cDNAs of 2-OST and 6-OST-1 were gifts from Dr. Rosenberg (Massachusetts Institute of Technology, Cambridge, Mass., U.S.A.) and Dr. Kimata (Aichi University, Japan), respectively. Expression of 2-OST and 6-OST was achieved in Rosetta-gami B (DE3) cells (Novagen, a brand of EMD Biosciences, San Diego, Calif., U.S.A.) using a standard procedure. Briefly, cells containing the plasmid expressing 2-OST or 6-OST were grown in Luria broth (LB) medium supplemented with 2 mg/ml glucose, 15 µg/ml tetracycline, 15 µg/ml kenamycin, 35 µg/ml chloramphenicol, and 50 µg/ml carbenicillin at 37° C. When the $A_{600}$ reached 0.6-0.8, Isopropyl-β-D-thiogalactopyranoside (1 mM) was added, and the cells were shaken overnight at 22° C. The bacteria were harvested, and the proteins were purified by following a protocol from the manufacturer (New England Biolabs). The purified proteins migrated at 75 kDa on 12% SDS-PAGE with the purity greater than 80%.

Preparation of 3-OST-1 bacterial expression plasmid (b3-OST-1-pET28). The cDNA fragment encoding the catalytic domain of 3-OST-1 (G48-H311) was amplified from m3-OST-1-pcDNA3 with a 5' overhang containing an NdeI site and a 3' overhang containing an EcoRI site. This construct was inserted into the pET28a vector (Novagen) using the NdeI and EcoRI restriction sites to produce a $(His)_6$-tagged protein. The resultant plasmid (b3-OST-1-pET28) was sequenced to confirm the reading frame and the lack of mutations within the coding region (University of North Carolina, DNA sequencing core facility). The plasmid, b3-OST-1-pET28, was transformed into BL21(DE3)RIL cells (Stratagene, La Jolla Calif., U.S.A) for the expression of 3-OST-1.

Protein expression and purification of 3-OST-1. Cells containing the b3-OST-1-pET28 were grown in twelve 2.8 L Fernbach flasks containing 1 L of LB media with 50 µg/mL of kanamycin at 37° C. When the $OD_{600}$ reached 0.6 to 0.8, the temperature was lowered to 22° C. for 15 min. Isopropyl-β-D-thiogalactopyranoside (IPTG) was then added to a final concentration of 200 µM, and the cells were allowed to shake overnight. Cells were pelleted and resuspended in 120 mL of sonication buffer, 25 mM Tris pH 7.5, 500 mM NaCl, and 10 mM imidizole. Cells were disrupted by sonication then spun down. The supernatant was applied to NTA-agarose resin (Qiagen, Valencia, Calif., U.S.A.) in batch and washed with sonication buffer. The resin was loaded onto a column and the protein was eluted with an imidizole gradient from 10 mM to 250 mM.

Preparation of 3-OST-3 expression plasmid. The cDNA fragment encoding the catalytic domain of 3-OST-3 (G139-G406) was amplified from plasmid h3-OST-3A-pcDNA3 (Liu, J. et al (1999) J. Biol. Chem. 274, 5185-5192) with a 5' overhang containing an NdeI site and a 3' overhang containing an EcoRI site. This construct was inserted into the pET28a vector (Novagen) using the NdeI and EcoRI restriction sites to produce a $(His)_6$-tagged protein. The resultant plasmid was sequenced to confirm the reading frame and the lack of mutations within the coding region (University of North Carolina, DNA sequencing core facility). The plasmid was transformed into BL21(DE3)RIL cells (Stratagene) for the expression of 3-OST-3.

Protein expression and purification of 3-OST-3. Cells containing the 3-OST-3 were grown in twelve 2.8 L Fernbach flasks containing 1 L of LB media with 50 µg/mL of kanamycin at 37° C. When the $OD_{600}$ reached 0.6 to 0.8, the temperature was lowered to 22° C. for 15 min. Isopropyl-β-D-thiogalactopyranoside (IPTG) was then added to a final concentration of 200 µM, and the cells were allowed to shake overnight. Cells were pelleted and resuspended in 120 mL of sonication buffer, 25 mM Tris pH 7.5, 500 mM NaCl, and 10 mM imidizole. Cells were disrupted by sonication then spun down. The supernatant was applied to NTA-agarose resin (Qiagen) in batch and washed with sonication buffer. The resin was loaded onto a column and the protein was eluted with an imidizole gradient from 10 mM to 250 mM.

Preparation of Immobilized HS Sulfotransferases. Dialyzed sulfotransferases (3 ml, 4 mg/ml) in phosphate-buffered saline buffer (3 mM KCl, 1.5 mM $KH_2PO_4$, 8 mM $Na_2HPO_4$, 138 mM NaCl, pH 7.2) were mixed with 1 ml of AMINOLINK® plus beads (Pierce, Rockford, Ill., U.S.A.) following a protocol from the manufacturer. Immobilized enzyme was washed with 50 mM MES, 1% Triton X-100, 1 mM $MgCl_2$, and 1 mM $MnCl_2$, pH 7.0, and stored at 4° C.

Measurement of Enzymatic Activities of Immobilized Proteins. To determine the activity of 3-OST-1 and 3-OST-3, HS from bovine kidney (ICN Biomedicals, Aurora, Ohio, U.S.A.) was used as a substrate; to determine the activity of 6-OST and 2-OST, CDSNS heparin was used as a substrate. Immobilized proteins (100 µl, ~300 µg of immobilized enzyme) with 100 µg of substrate (HS for 3-OST and CDSNS heparin for 2-OST or 6-OST) and 200 µM [$^{35}$S]PAPS (1000 cpm/pmol) in 1 ml of 50 mM MES, pH 7.0, 1% Triton X-100, 1 mM $MgCl_2$, and 1 mM $MnCl_2$. After rotating at room temperature for 1 h, the supernatant was collected, and the beads were washed with 3×200 µl of 1 M NaCl in 25 mM MOPS (pH 7.0). The supernatant and washes were combined, diluted with 2 ml of water, and subjected to DEAE chromatography to determine the amount of [$^{35}$S]HS product used to determine the activities of the various HS O-STs.

PAPS Regeneration System. The reactions involved in the PAPS regeneration system are shown in FIG. 1B. N-terminal $His_6$-tagged AST-IV was expressed in *E. coli* and purified as described by Burkat and colleagues (Burkart et al. (2000) *J. Org. Chem.* 65, 5565-5574) at a yield of ~50 mg/liter of bacterial culture. The full-length cDNA of rat AST-IV was a generous gift of Dr. Michael Duffel (University of Iowa) (Sheng et al. (2004) *Drug Metabol. Dispos.* 32, 559-565).

Modification of Polysaccharides. All enzymatic modifications, including those catalyzed by 2-OST, 6-OST, 3-OST-1, and 3-OST-3 followed the same protocol. Briefly, 20 mg of purified AST-IV was incubated with 40 µM PAP and 1 mM PNPS in 20 ml of 50 mM MES, pH 7.0, 1% Triton X-100, 1 mM $MgCl_2$, and 1 mM $MnCl_2$ at 25° C. for 15 min. The reaction mixture was mixed with 4 ml of immobilized sulfotransferase, 2 mg of a polysaccharide substrate was added, and the mixture was rotated at 25° C. for 24 h. The supernatant was recovered, and the polysaccharide that bound to the beads was eluted by washing three times with 8 ml of 1 M NaCl in 25 mM MOPS. Both the supernatant and wash were combined and the product was precipitated by adding ethanol (3 volumes). After incubating overnight at 4° C., polysaccharide was recovered by centrifugation.

Estimation of the Modification Level. The completion of 2-OST modification was monitored by incubating 10 μg of polysaccharide (Liu and Thorp (2002) *Med. Res. Rev.* 22, 1-25) with 20 μg of soluble 2-OST in the presence of 100 μM of [$^{35}$S]PAPS at 37° C. for 30 min. In a control experiment, 10 μg of compound 1 (FIG. 1A) replaced the previously modified polysaccharide in the otherwise identical reaction mixture. By comparing the amount of $^{35}$S incorporation, the extent of the original 2-O-sulfation reaction could be estimated. For monitoring the completion of 6-OST, compound 1 or 2 (FIG. 1A) was used as a substrate; for 3-OST-1, compound 4 was used (FIG. 1A).

Using [$^{35}$S]PAPS as a Sulfate Donor. Antithrombin (AT)-binding and gD-binding experiments utilized $^{35}$S-labeled polysaccharides prepared using [$^{35}$S]PAPS. In a typical reaction, 2 mg of HS substrate was incubated with 4 ml of beads with immobilized sulfotransferase (~12 mg of immobilized enzyme) at 25° C. in 20 ml of 50 mM MES, pH 7.0, 1% Triton X-100, 1 mM MgCl$_2$, and 1 mM MnCl$_2$, 200 μM [$^{35}$S]PAPS (1000 cpm/pmol) for 1 h. The resultant polysaccharide was recovered using DEAE chromatography.

Disaccharide Analysis. Synthesized polysaccharides (100 μg) were degraded by a mixture of heparin lyases as previously described (Moon et al. (2204) *J. Biol. Chem.* 279, 45185-45193) and desalted on BIOGEL® P-2 column (0.5× 200 cm; Bio-Rad Labs) in 0.1 M NH$_4$HCO$_3$. Disaccharides were analyzed by a C$_{18}$ reversed phase column (0.45×25 cm; Vydac, Columbia, Md., U.S.A.) with UV 232 detection and identified by coelution with appropriate standards (Chen et al. (2003) *Glycobiology* 13, 785-794). The overall recovery yield of the disaccharide analysis was estimated by using 2-O-[$^{35}$S]heparin (100,000 cpm/70 ng; compound 2) as an internal control.

NMR Analysis. Polysaccharide sample (1-2 mg) was dissolved in 0.5 ml of $^2$H$_2$O (99.9%), freeze dried to remove exchangeable protons, redissolved in 75 μl of $^2$H$_2$O (100.00%), and transferred to NMR microtubes (Shigemi, Inc., Allison Park, Pa., U.S.A.). NMR spectra were referenced relative to the HO$^2$H at 4.80 ppm, and in COSY water was suppressed by presaturation of the HO$^2$H resonance.

Determination of the Binding to AT and FGF2 Using Surface Plasmon Resonance Spectroscopy (SPR). Heparin and the synthesized polysaccharides were biotinylated as described (Hernaiz et al. (2000) *Biochem. Biophys. Res. Commun.* 276, 292-297). A solution of the biotinylated polysaccharides (0.1 mg/ml) in HEPES (10 mM), 0.15 M NaCl, 3 mM EDTA, and 0.005% surfactant P20 (HBS-EP) was flowed over the cells of the streptavidin chip at 5 μl/min. To determine the K$_D$ values, different concentrations (25-1600 nM in HBS-EP buffer) of FGF2 and AT were individually injected at 30 μl/min (running buffer: HBS-EP). Kinetic injection was used, leading the protein to flow for 180 seconds (s) and dissociated for the next 180 s, and the surface was regenerated by a 60 s injection of 30 μl of 2 M NaCl. Response units were monitored as a function of time to afford sensorgrams. The SPR curves for FGF2 fit well at individual concentrations, but the global fit suggested significant binding heterogeneity. Thus, the equilibrium response unit RU(eq) values from the sensorgrams of FGF2 binding to polysaccharide-containing surfaces were used to construct Scatchard plots, RU(eq)/C versus RU(eq), where C is the free protein concentration, resulting in linear, first degree polynomial functions confirming the one-to-one binding of FGF-polysaccharide and to estimate binding affinity. A two-state reaction model was applied to the AT-polysaccharide interactions measured by SPR using curve fitting to estimate the association and dissociation rate constants and affinity constant.

FGF2/FGFR1C-mediated Proliferation Assay. The BaF3 cells ectopically expressing FGFR1C have been previously described (Ornitz et al. (1996) *J. Biol. Chem.* 271, 15292-15297). The BaF3-FGFR1c cells were maintained in RPMI 1640 medium (Sigma Chemical Co., St. Louis, Mo., U.S.A.) supplemented with 10% fetal bovine serum, 0.5 ng/ml interleukin (IL)-3 (PeproTech Inc., Rocky Hill, N.J., U.S.A.), 2 mM L-glutamine, penicillin (50 IU/ml) and streptomycin (50 μg/ml), and 50 μM β-mercaptoethanol. For mitogenic assays, BaF3 FGFR1c cells were washed three times with RPMI 1640 medium to remove IL-3 and resuspended in the growth medium lacking IL-3. About 30,000 cells were plated per well in a 96-well plate in medium containing 1 μg/ml heparin, compound 1, 2, 3, 4a, or 4b, and 2 nM FGF-2 (PeproTech) in a total volume of 200 μl. The cells were then incubated at 37° C. for 40 h. To each well, an additional 50 μl of growth medium containing 1 μCi of [$^3$H]thymidine was added. Cells were harvested after 4-5 h by filtration through glass fiber paper. The incorporation of [$^3$H]thymidine into the DNA was determined by scintillation counting.

Determination of the Binding of Compounds 5-8 to AT. Approximately 1×10$^5$ cpm of $^{35}$S-labeled compound was incubated with 5 μg of human AT (Cutter Biological, Clayton, N.C., U.S.A.) in 50 μl of binding buffer containing 10 mM Tris-HCl, pH 7.5, 150 mM NaCl, 1 mM Mn$^{2+}$, 1 mM Mg$^{2+}$, 1 mM Ca$^{2+}$, 10 μM dextran sulfate, 0.0004% Triton X-100, and 0.02% sodium azide for 30 min at room temperature. Concanavalin A-Sepharose® (Sigma; 50 μl of 1:1 slurry. Sepharose is a high MW substance for gel filtration and chromotography, and a trademark of Pharmacia) was then added, and the reaction was shaken at room temperature for 1 h. The beads were then washed by 3×1 ml of binding buffer, and the bound polysaccharide was eluted with 1 M NaCl.

Inhibition Effect of the Polysaccharides on the Activities of Factor Xa and Thrombin. Assays were based on two previous methods (Zhang et al. (2001) *J. Biol. Chem.* 276, 42311-42321; Duncan et al. (2004) *Biochim. Biophys. Acta* 1671, 34-43). Briefly, factor Xa (Enzyme Research Laboratories, South Bend, Ind., U.S.A.) and thrombin (Sigma) were diluted to 20 and 8 units/ml with phosphate-buffered saline containing 1 mg/ml bovine serum albumin, respectively. AT was diluted with phosphate-buffered saline containing 1 mg/ml bovine serum albumin to give a stock solution at the concentration of 27 μM. The chromogenic substrates, S-2765 (for factor Xa assay) and S-2238 (for thrombin assay) were from Diapharma (West Chester, Ohio, U.S.A.) and made up at 1 mM with 1 mg/ml POLYBRENE® (Anti-heparin compound, Sigma) in water. The synthesized polysaccharide (compounds 5, 7, and 8; FIG. 1A) or heparin was dissolved in a buffer containing 50 mM Tris-HCl, pH 8.4, 7.5 mM Na$_2$EDTA, 175 mM NaCl at various concentrations (1-10, 000 ng/ml). The reaction mixture, which comprised 25 μl of AT stock solution and 25 μl of the solution containing polysaccharide, was incubated at 37° C. for 2 min. Factor Xa (25 μ) or thrombin (25 μl) was added. After incubating 37° C. for 4 min, 25 μl of S-2765 or S-2238 was added. The absorbance of the reaction mixture was measured at 405 nm continuously for 10 min. The absorbance values were plotted against the reaction time. The initial reaction rates as a function of concentration were used to calculate the $IC_{50}$ values. The concentrations of the synthesized polysaccharides were determined using Alcian blue as described by Bjornsson (Bjornsson (1993) *Anal. Biochem.* 210, 282-291) and quantitative disaccharide analysis as described above.

The Binding to Herpes Simplex Virus gD. The assay for determining binding of $^{35}$S-labeled polysaccharides (compounds 5 and 6; FIG. 1A) to gD was carried out by an immunoprecipitation procedure using anti-gD monoclonal antibody (DL6) (Shukla et al. (1999) *Cell* 99, 13-22).

EXAMPLE 1

Development of an Efficient Enzymatic Synthesis of Sulfated Polysaccharides

Expression of HS Sulfotransferases in *E. coli*. The presently disclosed subject matter provides methods for synthesizing biologically active HS, such as for example FGF-binding HS (e.g., compound 4, including 4a and 4b), AT-binding HS (e.g., compound 5), and herpes simplex virus gD-binding HS (e.g., compound 6). See FIG. 1A. Four enzymes, including 2-OST, 6-OST, 3-OST-1, and 3-OST-3, were utilized for the syntheses of these particular targets. Bacterial expressed 3-OST-1 and 3-OST-3 can exhibit substrate specificity and specific enzymatic activity comparable with those of their counterparts expressed in insect cells (Moon et al. (2004) *J. Biol. Chem.* 279, 45185-45193; Edavettal et al. (2004) *J. Biol. Chem.* 279, 25789-25797). Expression of the catalytic domains of 2-OST and 6-OST was also achieved in relatively high yield by preparing a fusion protein with MBP and 2-OST or 6-OST in Rosetta-gami B cells. Because 2-OST and 6-OST fusion proteins were enzymatically active and highly soluble, the MBP domain was retained.

Figure 2:
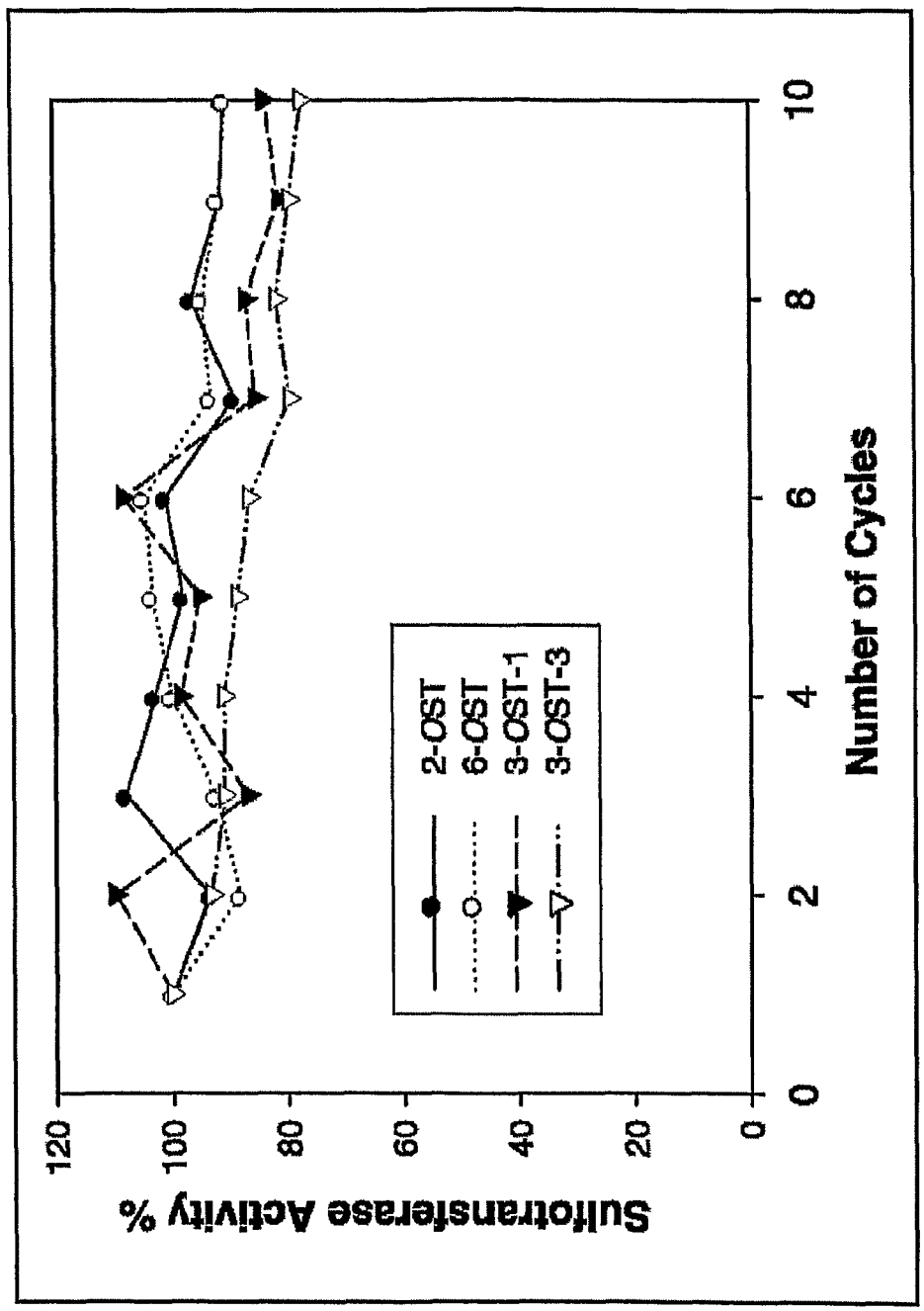
FIG. 2 is a graph showing activities of recycled immobilized sulfotransferases. The immobilized enzymes were utilized in multiple cycles. The activities of the immobilized enzymes after each cycle were determined as described in the Examples herein below. A total of 10 cycles was conducted. 2-OST (●); 6-OST (○); 3-OST-1 (▼); and 3-OST-3 (Δ).

Immobilized Enzymes are Reusable. 2-OST, 6-OST, 3-OST-1, and 3-OST-3 were immobilized on agarose to be reusable and to enhance the thermal stability. Immobilized enzymes were incubated with polysaccharide substrate and PAPS for 1 h at room temperature. The sulfated polysaccharide product was separated from the immobilized enzyme by washing the beads with 1 M NaCl followed by centrifugation, making the immobilized enzymes ready for the next synthetic cycle. The cycle was repeated 10 times, after which each of the immobilized enzymes were assayed and showed >80% of their catalytic activity (FIG. 2). It was also determined that the immobilized enzymes also maintained >65% of their catalytic activity after 2 months of storage at 8° C.

Introduction of PAPS Regeneration System. PAP inhibits sulfotransferase-catalyzed reactions. A PAPS regeneration system can be used to convert PAP to PAPS by relying on AST-IV to catalyze the transfer of the sulfo group from PNPS to PAP, as illustrated in FIG. 1B. The presently disclosed subject matter provides for the use of the PAPS regeneration system coupled with O-sulfotransferases. As disclosed herein, the PAPS regeneration system performed very well with 2-OST, 6-OST, and 3-OST-1. Complete modification of the substrate could be demonstrated by the low susceptibility of polysaccharide product to undergo additional sulfation using [$^{35}$S]PAPS with soluble enzymes, as disclosed herein above. Under the standard conditions, 2-OST, 6-OST, and 3-OST-1 afforded 98, 97, and 98% complete modification, respectively, using the PAPS regeneration system. These results demonstrate that the PAPS regeneration system functioned properly, providing sufficient PAPS for the complete sulfotransferase-catalyzed modification of polysaccharide substrates. This conclusion was further supported by characterizing the structures of the newly synthesized polysaccharide products 2, 3, 4a, 4b, and 5 (described herein below; see also FIG. 1A). In a parallel experiment, [$^{35}$S]PAPS was used as the sulfo donor to sulfate the polysaccharides in order to estimate the number of sulfo groups that were incorporated into the product. Six 2-O-sulfo and 6-O-sulfo groups and three 3-O-sulfo groups were estimated to be transferred to one polysaccharide molecule, respectively, assuming that the length of the polysaccharide is 25 disaccharide units. Approximately 1.5 mg of anticoagulant HS (5) was synthesized from 10 mg of CDSNS heparin (1) using immobilized sulfotransferases and the PAPS regeneration system.

EXAMPLE 2

Structural Characterization of Synthesized Polysaccharides

Figure 3:
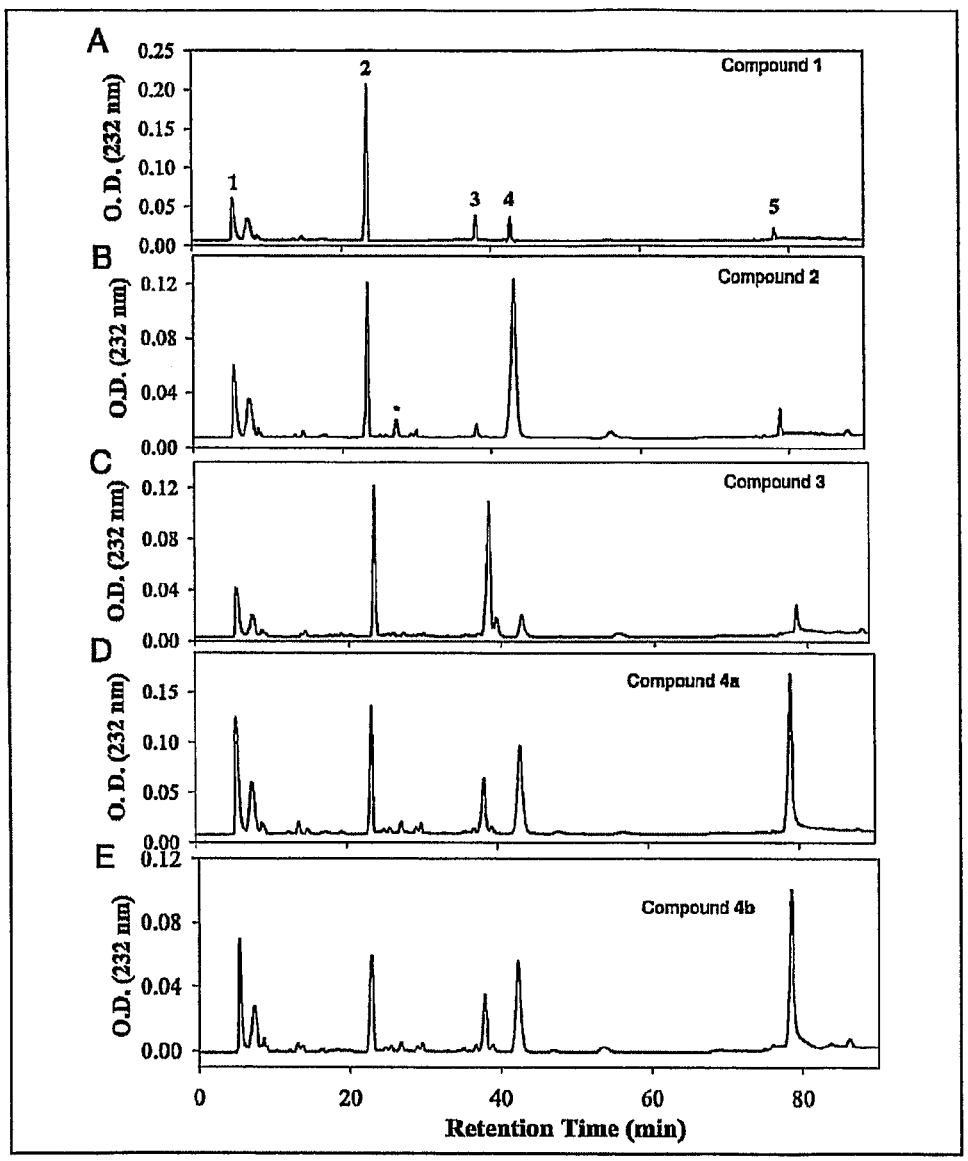
FIGS. 3A-3E are RPIP-HPLC chromatograms of the disaccharide analysis of synthesized polysaccharides. The synthesized polysaccharides were digested with a mixture of heparinases, including heparin lyase I, II, III, and heparinase IV. The resultant disaccharides were purified by BioGel P-2 and resolved on RPIP-HPLC.

Disaccharide Analysis of the Polysaccharides. Synthesized polysaccharide intermediates were digested with a mixture of heparin lyases, and the resulting disaccharides were analyzed using RPIP-HPLC (FIG. 3). As expected, analysis of compound 1 showed a disaccharide component of the structure of ΔUA-GlcNS (disaccharide 2), residual unsulfated disaccharide, Δ UA-GlcNAc (disaccharide 1), and small amounts of sulfated disaccharides (disaccharides 3-5) due to incomplete chemical desulfation (FIG. 3A and Table 2). The modification by 2-OST elevated the level of ΔUA2S-GlcNS (disaccharide 4) by about 5-fold (FIG. 3B and Table 2), confirming the structure of compound 2. Analysis of compound 3 afforded a 7-fold increase in the level of the disaccharide ΔUA-GlcNS6S (disaccharide 3) compared with compound 1, consistent with 6-OST-catalyzed modification (FIG. 3C and Table 2). The level of trisulfodisaccharide, ΔUA2S-GlcNS6S (disaccharide 5), in compounds 4a and 4b was increased by about 10-fold compared with that of compound 1 (FIGS. 3D and 3E, and Table 2). The results from the disaccharide analysis clearly establish that the expected enzymatic modifications took place at each step. It is interesting to note that 6-O-sulfation occurs at N-sulfoglucosamine, consistent with the substrate specificity of 6-OST in vitro (Smeds et al. (2003) *Biochem. J.* 372, 371-380). The 2-O-sulfation predominantly occurs at the uronic acid with an N-sulfoglucosamine residue at the reducing end. It is also noted that substantial amounts of ΔUA-GlcNS (disaccharide 2) remain in compounds 4a and 4b. This observation is not unexpected, since the HS from various tissues also afford a ΔUA-GlcNS aisaccnande unit, suggesting that the structures of compounds 4a and 4b are similar to HS from natural sources (Ledin et al. (2004) *J. Biol. Chem.* 279, 42732-42741).

TABLE 2

Summary of the disaccharide compositions of the synthetic polysaccharides

| Compound | ΔUA-GlcNAc nmol[a] % | ΔUA-GlcNS nmol % | ΔUA2S-GlcNS nmol % | ΔUA-GlcNS6S nmol % | ΔUA2S-GlcNS6S nmol % | Total recovery %[b] |
|---|---|---|---|---|---|---|
| 1 | 12.5 (16.1%) | 50.0 (64.4%) | 6.3 (8.1%) | 6.3 (8.1%) | 2.5 (3.2%) | 54.0 |
| 2 | 12.5 (16.6%) | 27.5 (36.6%) | 30.0 (40.0%) | 2.5 (3.3%) | 2.5 (3.3%) | 49.2 |
| 3 | 10.0 (14.0%) | 27.5 (38.5%) | 5.0 (7.0%) | 25.0 (35.0%) | 3.8 (5.3%) | 51.0 |
| 4a | 12.5 (18.8%) | 17.5 (26.2%) | 7.5 (11.2%) | 10.0 (15.0%) | 20.0 (30.0%) | 50.0 |
| 4b | 17.5 (21.7%) | 15.0 (18.6%) | 8.0 (9.9%) | 15.0 (18.6%) | 25.0 (31.0%) | 48.0 |

[a]The amount of each disaccharide was estimated by determining its peak area with a standard curve generated with a known amount of the disaccharide standard.
[b]A recovery yield was calculated by using 2-O-[$^{35}$S]sulfoheparin as an internal standard.

Each synthesized polysaccharide (100 μg) was digested with a mixture of heparin lyases. The resultant disaccharides were purified by a BioGel P-2 column and resolved by RPIP-HPLC.

NMR Analysis of the Polysaccharides. The $^1$H NMR analysis was conducted on the synthesized polysaccharides to allow assessment of their structures at the polymer levels as well as to estimate the composition. The assignment of each non-exchangeable proton was made using COSY, and their chemical shifts are reported in Table 3.

TABLE 3

$^1$H chemical shift data (in ppm) for the synthesized polysaccharides

| | GlcN H1 | GlcN H2 | GlcN H3 | GlcN H4 | GlcN H5 | GlcN H6a/b | IdoUA H1 | IdoUA H2 | IdoUA H3 | IdoUA H4 | IdoUA H5 |
|---|---|---|---|---|---|---|---|---|---|---|---|
| Heparin | 5.41 | 3.26 | 3.69 | 3.79 | 4.04 | 4.29 4.42 | 5.22 | 4.35 | 4.22 | 4.12 | 4.82 |
| compound 1 | 5.40 | 3.23 | 3.67 | 3.72 | 3.79 | 3.84 | 4.87 | 3.70 | 3.93 | 4.17 | 4.72 |
| compound 2 | 5.33 | 3.24 | 3.70 | 3.74 | 3.75-3.84 | 3.85 | 5.23 | 4.34 | 4.23 | 4.08 | 4.87 |
| compound 3 | 5.38 | 3.24 | 3.63 | 3.78 | 4.13 | 4.30 | 4.95 | 3.72 | 4.10 | 4.05 | 4.74 |
| compound 4a | 5.38 | 3.25 | 3.70 | 3.83 | 4.19 | 4.25 4.33 | 5.23 | 4.33 | 4.21 | 4.13 | 4.90 |
| compound 4b | 5.37 | 3.25 | 3.67 | 3.83 | 4.18 | 4.26 4.33 | 5.22 | 4.35 | 4.21 | 4.15 | 4.90 |
| compound 5 | 5.36 | 3.22 | 4.10 | 3.71 | 4.17 | 4.32 4.38 | 5.23 | 4.33 | 4.22 | 4.08 | 4.94 |

The integration of the N-acetyl signal in the $^1$H NMR of heparin was compared with the integration of the GlcNS-H1 signal, allowing estimation of the level of modifications. The ratio of these integrals showed that ~15% of the glucosamine residues contained N-acetyl groups. Using this information, the incorporation of 2-O-, 3-O-, and 6-O-sulfo groups was examined. Comparison of the N-acetyl peak with IdoUA2S-H2 in compound 2 demonstrates incorporation of a 2-O-sulfo group into 35% of the IdoUA residues. Based on this incorporation into compound 2, the integral of GlcNS-H6a and IdoUA2S-H2 (overlapping signal) was compared with the integral of the N-acetyl methyl group in compound 4a to estimate the level of incorporation of the 6-O-sulfo group. Integration showed that the 6-O-sulfo group was incorporated into 25% of the GlcNS residues. The reduced level of incorporation is not surprising, since only the 6-OST-1, and not 6-OST-2 and -3, was used in this synthesis. In compound 5, the incorporation of the 3-O-sulfo group was calculated by comparing the integral of the N-acetyl methyl group with GlcN-H3 and IdoUA-H4 (overlapping signal). Based on these calculations, the 3-O-sulfo group was incorporated into 32% of the GlcNS6S residues. According to $^1$H NMR and COSY experiments (Table 3), the structures of the compounds 4a, 4b, and 5 were all found to be similar to heparin and contained no unusual signals. Compound 5 showed a slightly greater heterogeneity, as evidenced by additional minor signals corresponding to additional 3-O-sulfo group-containing sequences in the $^1$H NMR, when compared with heparin. This is not unexpected, since heparin contains a lower level of 3-O-sulfo groups/chain than the content of 3-O-sulfo groups/chain observed in compound 5 as determined by $^{35}$S incorporation.

The composition estimated by NMR is consistent with the results of disaccharide analysis. NMR analysis suggests that about 15% of the glucosamine unit is N-acetylated, which is similar to the results of disaccharide analysis for ΔUA-GlcNAc (14-22%; Table 2). NMR analysis demonstrates that compound 2 comprises 35% of IdoUA2S-GlcNS, and compound 4a comprises 25% of IdoUA2S-GlcNS6S, and disaccharide analysis demonstrates that compounds 2 and 4a comprise 40% of ΔUA2S-GlcNS and 30% of ΔUA2S-GlcNS6S, respectively. Because of the signal overlap, the degree of 6-O-sulfation in compounds 3 and 4b using $^1$H NMR was not calculated.

EXAMPLE 3

Determination of the Biological Activities of the Synthesized Polysaccharides

The Binding of the Polysaccharides to AT and FGF2. Characterization of the affinities of AT to heparin and enzymatically modified heparin derivatives were performed by SPR. A two-state reaction model was applied to the SPR study of AT and polysaccharide interactions using BIAevaluation™ Software (Biacore Life Sciences, Uppsala, Sweden) for curve fitting analysis. None of the derivatives with the exception of the 2,6,3-O-sulfopolysaccharide (5) and heparin had high affinity to AT. The binding constant ($K_D$) for the binding of compound 5 to AT was determined to be 170 nM, which is very similar to that of heparin (75 nM). The binding affinity of FGF2 to the synthesized polysaccharides was also estimated. Compound 1 showed no interaction with FGF2, whereas compounds 4a and 4b showed the identical binding affinity to FGF2 at a $K_d$ of 35 nM, which is similar to heparin (22 nM) and is consistent with the value reported in the literature (Ibrahimi et al. (2004) *Biochemistry* 43, 4724-4730).

Figure 4:
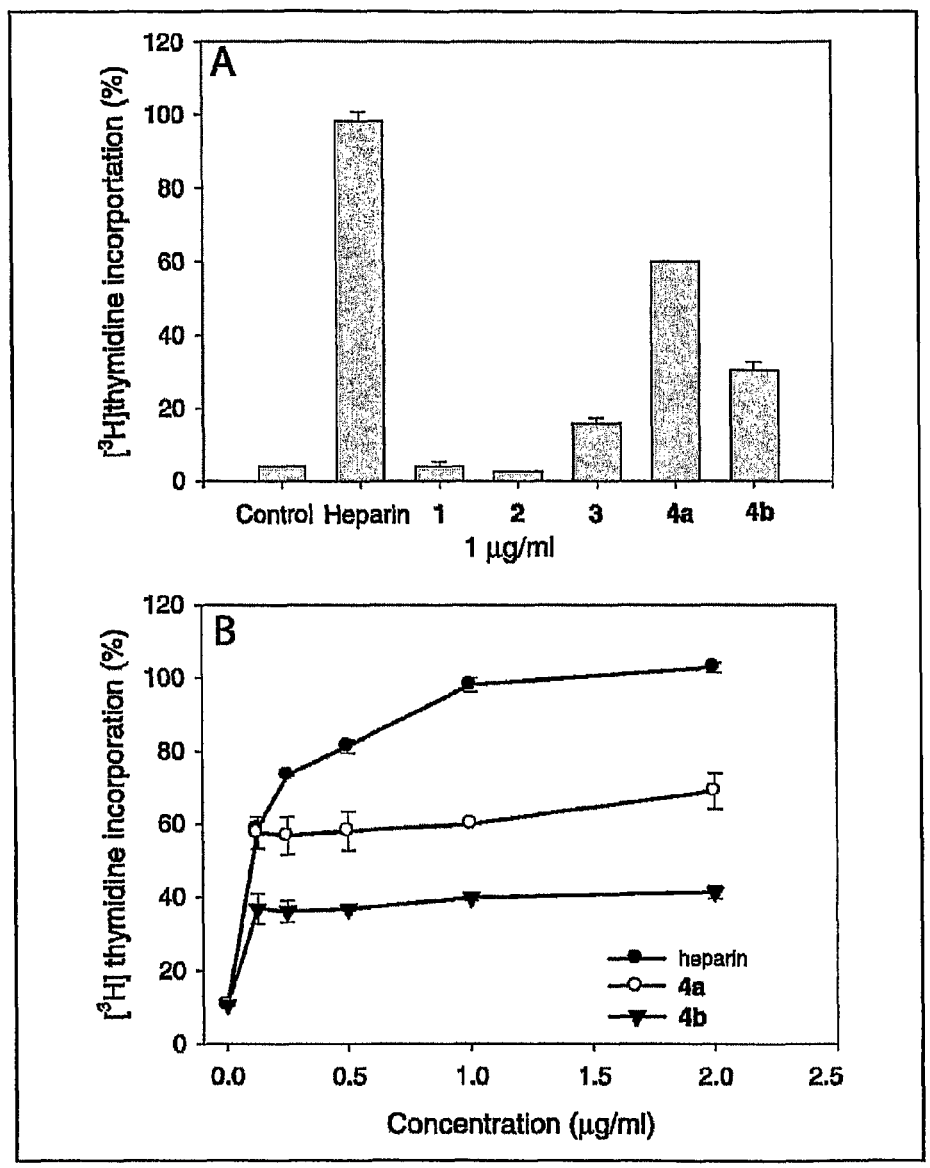
FIGS. 4A and 4B are graphs showing the effect of the synthesized polysaccharides on FGF-2-dependent BaF3 FGFR1c cell proliferation.

Synthetic Polysaccharides Promote Cell Proliferation. The BaF3 FGFR1c cells normally depend on IL-3 for growth. In the absence of IL-3, the cell proliferation depends on the addition of both FGF and heparin or HS (Ornitz et al. (1996) *J. Biol. Chem.* 271, 15292-15297). The activity of compounds 1, 2, 3, 4a, and 4b and heparin in promoting cell mitogenesis was measured using the FGF-2/FGFR1c system in BaF3 cells as described herein above. The cells receiving compounds 4a and 4b (at 1 μg/ml) showed an increase in [$^3$H]thymidine incorporation, which was about 60 and 40% of that of heparin, respectively, suggesting that the combinations of 2-O- and 6-O-sulfations confer the activity in promoting cell proliferation (FIG. 4A). The activity of 4a and 4b was also compared with that of heparin at different concentrations (FIG. 4B). It was found that compound 3 had moderate activity in promoting cell proliferation, whereas compounds 1 and 2 did not exhibit activity. The results are consistent with previously reported data on the contributions of the sulfo groups of HS to the mitogenic activity (Guimond and Turnbull (1999) *Curr. Biol.* 9, 1343-1346; Pye et al. (1998) *J. Biol. Chem.* 273, 22936-22942). It is noted that 4a appears to have stronger activity in promoting cell proliferation than 4b, suggesting that different sequences are generated by the different order of 2-O- and 6-O-sulfation as suggested by Jacobsson and Lindahl (Jacobsson and Lindahl (1980) *J. Biol. Chem.* 255, 5094-5100). However, such sequence difference could not be detected by the disaccharide or NMR analysis.

The Anticoagulant Activity of the Synthesized Polysaccharides. Heparin achieves its anticoagulant activity by forming a 1:1 complex with AT, which inhibits the activities of factor Xa and thrombin (Rosenberg et al. (1997) *J. Clin. Invest.* 99, 2062-2070). Because it is known that the introduction of the 3-O-sulfo group by 3-OST-1 is essential for the synthesis of anticoagulant HS, different types of 3-O-sulfo group-containing polysaccharides, compounds 5, 7, and 8, were prepared and their activities in inhibiting factor Xa and thrombin tested (Table 4). As expected, heparin is a potent activator for AT-mediated inhibition of factor Xa and thrombin, whereas ARIXTRA® (Fondaparinux, a low molecular weight heparin-like compound, GlaxoSmithKline) specifically activates the AT-mediated inhibition of factor Xa (Petitou and van Boeckel (2004) *Angew. Chem. Int. Ed.* 43, 3118-3133). Compound 5 has very similar potency to heparin, inhibiting the activities of both factor Xa and thrombin, suggesting that the presently disclosed enzyme-based approach is indeed capable of synthesizing the anticoagulant polysaccharide. It has been reported that the presence of 2-O-sulfo groups is not essential for HS binding to AT and its resulting anticoagulant activity (Zhang et al. (2001) *J. Biol. Chem.* 276, 28806-28813). Indeed, polysaccharide intermediate compound 8 lacks 2-O-sulfo groups but still exhibits anticoagulant activity, consistent with this previous report (Zhang et al. (2001) *J. Biol. Chem.* 276, 28806-28813). In contrast, compound 7 lacks 6-O-sulfo groups and, thus, has no anticoagulant activity, since 6-O-sulfo groups are critical in AT binding (Atha et al. (1985) *Biochemistry* 24, 6723-6729). Another 3-O-sulfated polysaccharide (compound 6) was also prepared to test for its anti-Xa and antithrombin activities. It is important to note that both compounds 5 and 6 carry a 3-O-sulfoglucosamine unit, although it is located in different saccharide sequences (FIG. 1A). It is known that 3-OST-3-modified HS does not bind to AT (Liu et al. (1999) *J. Biol. Chem.* 274, 5185-5192). As expected, compound 6 does not exhibit any anti-Xa and antithrombin activities. The binding of AT to the synthesized compounds was also measured (Table 4). It is clear that the anticoagulant activities of the compounds correlated to their binding affinity to AT. Taken together, these results demonstrate that the anticoagulant activities of these enzymatically synthesized polysaccharides are consistent with the known structure activity relationship of HS.

TABLE 4

Anti-factor Xa and antithrombin activities of synthesized polysaccharide intermediates

| Sample | Factor Xa inhibition $(IC_{50})^a$ ng/ml | Thrombin inhibition $(IC_{50})^a$ ng/ml | Binding to $AT^b$ % |
|---|---|---|---|
| Heparin$^c$ | 20 | 10 | ND$^d$ |
| Heparan sulfate$^e$ | >5000 | >3000 | ND |
| Arixtra$^f$ | 58 | >3000 | ND |
| Compound 7 | >2000 | >3000 | 5 |
| Compound 8 | 126 | 96 | 31 |
| Compound 5 | 40 | 32 | 38 |
| Compound 6 | >2000 | >2000 | 2 |

$^a$The procedures for measuring the activities of factor Xa and thrombin are described under "Experimental Procedures."
$^b$3-O-[$^{35}$S]sulfo compounds were used to determine their bindings to AT as described under "Experimental Procedures." $^3$H-Labeled HS from CHO cells was used as a negative control for the AT binding. About 0.3% of $^3$H-labeled HS bound to AT.
$^c$Heparin was from Sigma.
$^d$ND, not determined.
$^e$Heparan sulfate was isolated from bovine kidney.
$^f$Arixtra is the chemically synthesized antithrombin-binding pentasaccharide, which was obtained from a local pharmacy.

Preparation of the Polysaccharide That Binds to Herpes Simplex Virus gD. Herpes simplex virus utilizes HS as a receptor to infect the target cells (Shukla and Spear (2001) *J. Clin. Invest.* 108, 503-510). A specific 3-O-sulfo group-containing HS, generated by 3-OST-3, -5, or -6, serves as an entry receptor for herpes simplex virus type 1 through HS binding of gD (Shukla et al. (1999) *Cell* 199, 13-22; Xia et al. (2002) *J. Biol. Chem.* 277, 37912-37919; Xu et al. (2005) *Biochem. J.* 385, 451-459). Structural characterization of the gD-binding site revealed a unique octasaccharide sequence carrying a 3-O-sulfo glucosamine residue (Liu et al. (2002) *J. Biol. Chem.* 277, 33456-33467). To test if the presently disclosed enzymatic approach synthesizes gD-binding HS, compound 4 (FIG. 1A) was incubated with immobilized 3-OST-3 to generate compound 6 (FIG. 1A). It was found that 12% of the resultant polysaccharide (compound 6) bound to gD, whereas only 2.6% of compound 5, a 3-OST-1-modified polysaccharide, bound to gD as determined by immunoprecipitation (Table 5). Comparison with the appropriate controls showed that the percentage binding for 3-OST-3-modified HS closely resembled that of compound 6. In conclusion, the results suggest that the presently disclosed enzymatic approach is capable of effectively synthesizing gD-specific binding HS. It should be noted that commercial heparin does not bind to gD, and heparin is not a substrate for 3-OST-3 (Nicola et al. (1996) *J. Virol.* 70, 3815-3822; Liu et al. (1999) *J. Biol. Chem.* 274, 38155-38162). Therefore, these results also demonstrate that it is possible to redesign the sulfation patterns by first solvolytically removing all O-sulfo groups and then selectively enzymatically replacing sulfo groups required for specific interactions.

TABLE 5

The binding of synthesized polysaccharides to gD

| Sample | gD binding % |
| --- | --- |
| Unmodified HS[a] | 1.0 |
| 3-OST-1-modified HS[b] | 2.6 |
| 3-OST-3-modified HS[b] | 12.0 |
| Compound 5 | 2.6 |
| Compound 6 | 12.1 |

[a] [$^3$H]HS (from CHO cells) was prepared by metabolically labeling the cells with [$^3$H] glucosamine.
[b] 3-OST-1- and 3-OST-3-modified HS were prepared by incubating [$^3$H]HS with purified 3-OST-1 or 3-OST-3 enzymes.

Discussion of Examples 1-3

HS, including heparin, has a wide range of biological activities, including anticoagulation, antiviral, and anticancer activities. Sulfo group-containing saccharide sequences dominate the specificity of the functions of heparin and HS. Thus, the synthesis of a polysaccharide with the appropriate positioning of these functional groups to carry out its unique biological activity is desirable. The presently disclosed subject matter provides an approach to synthesize sulfo group-containing HS polysaccharides that have desired biological activities, including for example HS that binds to FGF2, herpes simplex virus gD, or AT. These HS polysaccharides can also demonstrate appropriate biological activity, such as anticoagulant activity mediated through AT binding and the activity in promoting cell proliferation. More importantly, the presently disclosed subject matter permits the synthesis of greater than 1 mg amounts of specific sulfo group-containing polysaccharides, sufficient for testing their activities in biochemical and biological assays. The quantities synthesized are also sufficient for extensive structural analysis, including disaccharide analysis and one- and two-dimensional NMR analysis.

In examples 1-3. two approaches were used to increase the scale of enzymatic synthesis. First, HS sulfotransferases were expressed in E. coli, readily affording 20-50 mg of purified enzymes. It has been shown that both 3-OST-1 and 3-OST-3 can be expressed in E. coli in relatively high yield. The presently disclosed subject matter also provides for the expression in E. coli of both 2-OST and 6-OST as the soluble 2-OST and 6-OST-MBP fusion proteins. Second, efficiency of enzymatic sulfation was improved by utilizing immobilized O-sulfotransferases and coupling their use to a PAPS regeneration system.

When a PAPS regeneration system was previously applied for preparing N-sulfoheparosan from heparosan using N-deacetylase/N-sulfotransferase, the N-sulfation yield was lower than that obtained using added exogenous PAPS (Saribas et al. (2004) Glycobiology 14, 1217-1228). Nevertheless, coupling of a PAPS regeneration system to enzymatic sulfation of polysaccharides, as disclosed herein, was considered a desirable goal for several reasons. First, PAP inhibits HS O-sulfotransferase activities with $IC_{50}$ values of ~100 µM under the reaction conditions used in the presently disclosed syntheses, making milligram-scale synthesis difficult without continuously removing PAP. Second, a PAPS regeneration system would permit use of PNPS as the sulfo donor and require only catalytic amounts of PAP, significantly reducing the cost of synthesis. The listed price of PNPS in the Aldrich catalog is about 300-fold less than PAPS. The immobilized enzyme format facilitates use of the enzymes repeatedly, making the method amendable to a large scale synthesis, since scale-up of immobilized enzyme columns is generally known in the art.

Developing an effective approach to synthesize HS is also desirable for understanding the mechanism of its biosynthesis. Unlike protein biosynthesis, polysaccharide biosynthesis is not a template-driven process. Although the cDNAs encoding the HS biosynthetic enzymes have been cloned, the genetic regulation mechanism for the synthesis of the HS with defined biological functions is not fully understood. The unique and often remote sequence features in substrate can influence the action of HS O-sulfotransferases. Furthermore, whether additional factors or the formation of complexes of biosynthetic enzymes takes part in controlling the structure of HS remains to be elucidated. It is interesting to note that a complex of HS epimerase and 2-OST in vivo has been reported (Pinhal et al. (2001) Proc. Natl. Acad. Sci. U.S.A. 98, 12984-12989). The presently disclosed approach provides a tool to answer these questions, since it is capable of generating a sufficient amount of HS product required for extensive structural biochemical and biological analysis.

HS is believed to be present in block structures, comprising highly sulfated and non-sulfated domains (Gallagher, J. T. (2001) J. Clin. Invest. 108, 357-361), and the HS with the biological activities largely contain the highly sulfated domains. Without wishing to be limited by theory, it is believed that the modifications in the present system indeed happen in a block fashion based on the following facts. First, the results of the disaccharide analysis concluded that both 6-O-sulfation and 2-O-sulfation are carried out predominantly in the sulfated region (FIG. 3 and Table 2). Second, the enzymatically-modified products exhibit the anticipated biological functions, including the activation of FGF/FGF receptor signaling (compounds 4a and 4b), carrying anticoagulant activity (compound 5), and binding to herpes simplex virus glycoprotein D (compound 6). Because the HS carrying these functions must contain the domain structures with a size larger than pentasaccharide (Petitou and van Boeckel (2004) Angew. Chem. Int. Ed. 43, 3118-3133; Atha et al. (1985) Biochemistry 24, 6723-6729; Liu et al. (2002) J. Biol. Chem. 277, 33456-33467; Maccarana et al. (1993) J. Biol. Chem. 268, 23898-23905), the synthetic products with the desired functions suggest that the modifications indeed occur in a block fashion.

In summary, the presently disclosed subject matter provides a method for enzymatic sulfation and preparation of HS with distinct biological activities. Unique sulfated saccharide sequences play a dominant role in the function and specificity of HS/heparin. The presently disclosed methods demonstrate the capability of using a collection of HS biosynthetic enzymes to synthesize HS/heparin with selected biological activities. The synthetic scale with this method can be easily increased for large scale synthesis, provided that both the enzymes and the sulfo donor are easily accessible. The current method clearly demonstrates that HS/heparin having specific biological activities can be synthesized by subjecting a backbone saccharide polymer to different enzymatic modifications. This enzymatic selectivity is currently not accessible by chemical sulfation approaches. The presently disclosed method can significantly aid the exploration of new potential therapeutic applications for HS. In addition, enzymatic synthesis of anticoagulant heparin can potentially lead to a better anticoagulant drug by reducing its side effects.

References

The references listed below as well as all references cited in the specification are incorporated herein by reference to the extent that they supplement, explain, provide a background for or teach methodology, techniques and/or compositions employed herein.

Aikawa et al., (1999) *J. Biol. Chem.* 274, 2690.
Aikawa, J.-I., et al., (2001) *J. Biol. Chem.* 276, 5876-5882.
Alexander, C. M., et al., (2000) *Nat. Genet.* 25, 329-332.
Altschul et al. (1990) *J Mol Biol* 215, 403-410.
Atha, D. H., Lormeau, J.-C., Petitou, M., Rosenberg, R. D., and Choay, J. (1985) *Biochemistry* 24, 6723-6729.
Avci, F. Y., Karst, N. A., and Linhardt, R. J. (2003) *Curr. Pharm. Des.* 9, 2323-2335.
Balagurunathan, K., Beeler, D. L., Lech, M., Wu, Z. L., and Rosenberg, R. D. (2003) *J. Biol. Chem.* 278, 52613-52621.
Balagurunathan, K., Lech, M. Z., Beeler, D. L., Wu, Z. L., and Rosenberg, R. D. (2003) *Nat. Biotechnol.* 21, 1343-1346.
Bernfield, M., et al., (1999) *Annu. Rev. Biochem.* 68, 729-777.
Bjornsson, S. (1993) *Anal. Biochem.* 210, 282-291.
Bowman et al., (1999) *Chem. Biol.* 6, R9-R22.
Burkart, M. D., Izumi, M., Chapman, E., Lin, C., and Wong, C. (2000) *J. Org. Chem.* 65, 5565-5574.
Capila, I., and Linhardt, R. J. (2002) *Angew. Chem. Int. Ed.* 41, 390-412.
Carfi, A., et al., (2001) *Mol. Cell.* 8:169-179.
Chen et al., (1992) *Protein Expression Purif.* 3, 421-6.
Chen, J., Duncan, M. B., Carrick, K., Pope, M., and Liu, J. (2003) *Glycobiology* 13, 785-794.
Dementiev, A., Petitou, M., Herbert, J.-M., and Gettins, P. G. (2004) *Nat. Struct. Biol.* 11, 867-863.
Dooley (1998) *Chemico-Biol. Interact.* 109, 29.
Duncan, M. B., Chen, J., Krise, J. P., and Liu, J. (2004) *Biochim. Biophys. Acta* 1671, 34-43.
Edavettal, S. C., Lee, K. A., Negishi, M., Linhardt, R. J., Liu, J., and Pedersen, L. C. (2004) *J. Biol. Chem.* 279, 25789-25797.
Esko, J. D., and Lindahl, U. (2001) *J. Clin. Invest.* 108:169-173.
Esko, J. D., and Selleck, S. B. (2002) *Annu. Rev. Biochem.* 71, 435-471.
Falany (1997) *FASEB J.* 11, 1-2.
Fukuta et al. (1998) *Biochim. Biophys. Act.* 1399, 57.
Gallagher, J. T. (2001) *J. Clin. Invest.* 108, 357-361.
Gribskov et al. (1986) *Nuc Acids Res* 14(1), 327-334.
Guimond, S. E., and Turnbull, J. E. (1999) *Curr. Biol.* 9, 1343-1346.
Guo et al. (1994) *Chem.-Biol. Interact.* 92, 25-31.
Habuchi et al., (1998) *J. Biol. Chem.* 273, 9208.
Habuchi, H., et al., (2000) *J. Biol. Chem.* 275, 2859-2868.
Hernaiz, M., Liu, J., Rosenberg, R. D., and Linhardt, R. J. (2000) *Biochem. Biophys. Res. Commun.* 276, 292-297.
Holmborn, K., Ledin, J., Smeds, E., Eriksson, I., Kusche-Gullberg, M., and Kjellen, L. (2004) *J. Biol. Chem.* 279, 42355-42358.
Ibrahimi, O. A., Zhang, F., Lang, S., Hrstka, C., Mohammadi, M., and Linhardt, R. J. (2004) *Biochemistry* 43, 4724-4730.
Jacobsson, I., and Lindahl, U. (1980) *J. Biol. Chem.* 255, 5094-5100.
Krummenacher, C., et al., (1999) *J. Virol.* 73, 8127-8137.
Kuberan, B., Beeler, D. L., Lawrence, R., Lech, M., and Rosenberg, R. (2003) *J. Am. Chem. Soc.* 125, 12424-12425.
Kyte et al. (1982) *J Mol Biol* 157, 105.
Ledin, J., Staatz, W., Li, J.-P., Gotte, M., Selleck, S. B., Kjellen, L., and Spillmann, D. (2004) *J. Biol. Chem.* 279, 42732-42741.
Lin et al., (1995) *J. Am. Chem. Soc.* 117, 8031.
Lin et al. (1998) *Anal. Biochem.* 264, 111-117.
Lindahl, U., et al., (1998) *J. Biol. Chem.* 273, 24979-24982.
Lindahl, U., Li, J., Kusche-Gullberg, M., Salmivirta, M., Alaranta, S., Veromaa, T., Emies, J., Roberts, I., Taylor, C., Oreste, P., Zoppetti, G., Naggi, A., Torri, G., and Casu, B. (2005) *J. Med. Chem.* 48, 349-352.
Linhardt, R. J. (2003) *J. Med. Chem.* 46, 2551-2564.
Liu, J., and Thorp, S. C. (2002) *Med. Res. Rev.* 22, 1-25.
Liu, J., et al., (1996) *J. Biol. Chem.* 271, 27072-27082.
Liu, J., et al., (1999) *J. Biol. Chem.* 274, 38155-38162.
Liu, J., et al., (1999) *J. Biol. Chem.* 274, 5185-5192.
Liu, J., Shworak, N. W., Sinaÿ, P., Schwartz, J. J., Zhang, L., Fritze, L. M. S., and Rosenberg, R. D. (1999) *J. Biol. Chem.* 274, 5185-5192.
Liu, J., Shriver, Z., Blaiklock, P., Yoshida, K., Sasisekharan, R., and Rosenberg, R. D. (1999) *J. Biol. Chem.* 274, 38155-38162.
Liu, J., Shriver, Z., Pope, R. M., Thorp, S. C., Duncan, M. B., Copeland, R. J., Raska, C. S., Yoshida, K., Eisenberg, R. J., Cohen, G., Linhardt, R. J., and Sasisekharan, R. (2002) *J. Biol. Chem.* 277, 33456-33467.
Liu, J., et al., (2002) *J. Biol. Chem.* 277, 33456-33467.
Maccarana, M., Casu, B., and Lindahl, U. (1993) *J. Biol. Chem.* 268, 23898-23905.
Marcus et al. (1980) *Aial. Biochem.* 107, 296.
Marshall et al., (1997) *J. Biol. Chem.* 272, 9153-9160.
Marshall et al., (1998) *Chem. -Biol. Interact.* 109, 107-116.
Mazany et al., (1998) *Biochim. Biophys. Act.* 1407, 92.
Moon, A., Edavettal, S. C., Krahn, J. X., Munoz, E. M., Negishi, M., Linhardt, R. J., Liu, J., and Pedersen, L. C. (2004) *J. Biol. Chem.* 279, 45185-45193.
Nastuk et al. (1998) *J. Neuroscience* 18, 7167.
Needleman et al. (1970) *J Mol Biol* 48, 443.
Nicola, A. V., Willis, S. H., Naidoo, N. N., Eisenberg, R. J., and Cohen, G. H. (1996) *J. Virol.* 70, 3815-3822.
Ong et al., (1998) *J. Biol. Chem.* 273, 5190.
Ornitz, D. M., Xu, J., Colvin, J. S., McEwen, D. G., MacArthur, C. A., Coulier, F., Gao, G., and Goldfarb, M. (1996) *J. Biol. Chem.* 271, 15292-15297.
Ouyang et al., (1998) *J. Biol. Chem.* 273, 24770.
Ozawa et al., (1990) *Nucleic Acids Res.* 18, 4001z.
Petitou, M., Herault, L.-P., Bernat, A., Driguez, P.-A., Duchaussoy, P., Lormeau, J.-C., and Herbert, J.-M. (1999) *Nature* 398, 417-422.
Petitou, M., and van Boeckel, C. A. A. (2004) *Angew. Chem. Int. Ed.* 43, 3118-3133.
Pinhal, M. A., Smith, B., Olson, S., Aikawa, J., Kimata, K., and Esko, J. D. (2001) *Proc. Natl. Acad. Sci. U.S.A.* 98, 12984-12989.
Pye, D. A., Vives, R. R., Turnbull, J. E., Hyde, P., and Gallagher, J. T. (1998) *J. Biol. Chem.* 273, 22936-22942.
Reizes, O., et al., (2001) *Cell* 106:105-116.
Rosenberg, R. D., et al., (1997) *J. Clin. Invest.* 99, 2062-2070.
Saeki et al. (1998) *J. Biochem.* 124, 55.
Sambrook et al. (2001) *Molecular Cloning: A Laboratory Manual*, Third Edition, Cold Spring Harbor Laboratory Press, Cold Spring Harbor, N.Y.
Saribas, A. S., Mobasseri, A., Pristatsky, P., Chen, X., Barthelson, R., Hakes, D., and Wang, J. (2004) *Glycobiology* 14, 1217-1228.
Sasisekharan, R., Shriver, Z., Venkataraman, G., and Narayanasami, U. (2002) *Nat. Rev. Cancer* 2, 521-528.
Schwartz et al. (1979) *Nuc Acids Res* 6(2), 745-755.
Sheng, J. J., Saxena, A., and Duffel, M. W. (2004) *Drug Metabol. Dispos.* 32, 559-565.
Shukla, D., et al., (1999) *Cell* 199, 13-22.
Shukla, D., and Spear, P. G. (2001) *J. Clin. Invest.* 108, 503-510.

Shworak, N. W., et al., (1997) *J. Biol. Chem.* 272, 28008-28019.
Smeds, E., Habuchi, H., Do, A.-T., Hjertson, E., Grundberg, H., Kimata, K., Lindahl, U., and Kusche-Gullberg, M. (2003) *Biochem. J.* 372, 371-380.
Smith et al. (1981) *Adv Appl Math* 2, 482.
Thompson et al. (1994) *Nucleic Acids Res* 22(22), 4673-4680.
U.S. Pat. No. 6,255,088.
Uchimura et al. (1998) *J. Biol. Chem.* 273, 22577.
Yoshinari et al., (1998) *J. Biochem.* 123, 740.
Wethmur & Davidson (1968) *J Mol Biol* 31, 349-370.
Willis, S. H., et al., (1998) *J. Virol.* 72, 5938-5947.
WuDunn, D., and Spear, P. G. (1989) *J. Virol.* 63, 52-58.
Xia, G., Chen, J., Tiwari, V., Ju, W., Li, J.-P., Malmström, A., Shukla, D., and Liu, J. (2002) *J. Biol. Chem.* 277, 37912-37919.
Xu, D., Tiwari, V., Xia, G., Clement, C., Shukla, D., and Liu, J. (2005) *Biochem. J.* 385, 451-459.
Yang et al. (1996) *Protein Expression Purif.* 8, 423-429.
Yang et al., (1997) *Protein Eng.* 10, 70.
Yang et al., (1998) *Chem. -Biol. Interact.* 109, 129-135.
Yoshinari et al., (1998) *J. Biochem.* 123, 740.
Zhang, L., Beeler, D. L., Lawrence, R., Lech, M., Liu, J., Davis, J. C., Shriver, Z., Sasisekharan, R., and Rosenberg, R. D. (2001) *J. Biol. Chem.* 276, 42311-42321.
Zhang, L., Lawrence, R., Schwartz, J. J., Bai, X., Wei, G., Esko, J. D., and Rosenberg, R. D. (2001) *J. Biol. Chem.* 276, 28806-28813.

It will be understood that various details of the presently disclosed subject matter can be changed without departing from the scope of the presently disclosed subject matter. Furthermore, the foregoing description is for the purpose of illustration only, and not for the purpose of limitation.

---

What is claimed is:

1. A method of preparing heparin from a first polysaccharide comprised of 1-4 glycosidically linked alternating polymer of uronic acid and glucosamine residues, wherein the uronic acid is selected from iduronic and glucuronic acid, wherein the glucosamine is partially N-sulfated; the method comprising
    (a) treating the first polysaccharide with a reaction mixture comprising recombinant 2-O-sulfotransferase (OST) enzyme comprising the amino acid sequence of SEQ ID NO: 1, to yield a second polysaccharide;
    (b) treating the second polysaccharide with a reaction mixture comprising recombinant 6-O-sulfotransferase (OST) enzyme to yield a third polysaccharide;
    (c) treating the third polysaccharide with a reaction mixture comprising recombinant 3-O-sulfotransferase (OST) enzyme isoform 1 to yield heparin;
    wherein in each of steps (a)-(c) the reaction mixture further comprises 3'-phosphoadenosine 5'-phosphosulfate (PAPS), an arylsulfotransferase and an aryl sulfate.

2. The method of claim 1, wherein the arylsulfotransferase is arylsulfotransferase IV and the aryl sulfate is p-nitrophenol sulfate (PNPS).

3. The method of claim 1, wherein said incubating is for from about 1 minute to about 30 minutes.

4. The method of claim 1, wherein the recombinant 6-O-sulfotransferase (OST) comprises the amino acid sequence selected from SEQ ID NOs 5, 6 or 7.

5. The method of claim 1, wherein the recombinant 3-O-sulfotransferase (OST) isoform 1 comprises the amino acid sequence of SEQ ID NO: 2.

6. The method of claim 5, wherein the recombinant 6-O-sulfotransferase (OST) comprises the amino acid sequence selected from SEQ ID NOs 5, 6 or 7.

\* \* \* \* \*

SEQUENCE LISTING

<160> NUMBER OF SEQ ID NOS: 8

<210> SEQ ID NO 1
<211> LENGTH: 356
<212> TYPE: PRT
<213> ORGANISM: Mus musculus

<400> SEQUENCE: 1

```
Met Gly Leu Leu Arg Ile Met Met Pro Pro Lys Leu Gln Leu Leu Ala
1               5                   10                  15

Val Val Ala Phe Ala Val Ala Met Leu Phe Leu Glu Asn Gln Ile Gln
            20                  25                  30

Lys Leu Glu Glu Ser Arg Ala Lys Leu Glu Arg Ala Ile Ala Arg His
        35                  40                  45

Glu Val Arg Glu Ile Glu Gln Arg His Thr Met Asp Gly Pro Arg Gln
    50                  55                  60

Asp Ala Thr Leu Asp Glu Glu Asp Ile Ile Ile Ile Tyr Asn Arg
65                  70                  75                  80

Val Pro Lys Thr Ala Ser Thr Ser Phe Thr Asn Ile Ala Tyr Asp Leu
                85                  90                  95

Cys Ala Lys Asn Arg Tyr His Val Leu His Ile Asn Thr Thr Lys Asn
            100                 105                 110

Asn Pro Val Met Ser Leu Gln Asp Gln Val Arg Phe Val Lys Asn Ile
        115                 120                 125

Thr Thr Trp Asn Glu Met Lys Pro Gly Phe Tyr His Gly His Ile Ser
    130                 135                 140

Tyr Leu Asp Phe Ala Lys Phe Gly Val Lys Lys Lys Pro Ile Tyr Ile
145                 150                 155                 160

Asn Val Ile Arg Asp Pro Ile Glu Arg Leu Val Ser Tyr Tyr Tyr Phe
                165                 170                 175

Leu Arg Phe Gly Asp Asp Tyr Arg Pro Gly Leu Arg Arg Lys Gln
            180                 185                 190

Gly Asp Lys Lys Thr Phe Asp Glu Cys Val Ala Glu Gly Gly Ser Asp
        195                 200                 205

Cys Ala Pro Glu Lys Leu Trp Leu Gln Ile Pro Phe Phe Cys Gly His
    210                 215                 220

Ser Ser Glu Cys Trp Asn Val Gly Ser Arg Trp Ala Met Asp Gln Ala
225                 230                 235                 240

Lys Ser Asn Leu Ile Asn Glu Tyr Phe Leu Val Gly Val Thr Glu Glu
                245                 250                 255
```

```
Leu Glu Asp Phe Ile Met Leu Glu Ala Ala Leu Pro Arg Val Phe
                260                 265                 270

Arg Gly Ala Thr Asp Leu Tyr Arg Thr Gly Lys Lys Ser His Leu Arg
            275                 280                 285

Lys Thr Thr Glu Lys Lys Leu Pro Thr Lys Gln Thr Ile Ala Lys Leu
            290                 295                 300

Gln Gln Ser Asp Ile Trp Lys Met Glu Asn Glu Phe Tyr Glu Phe Ala
305                 310                 315                 320

Leu Glu Gln Phe Gln Phe Ile Arg Ala His Ala Val Arg Glu Lys Asp
                325                 330                 335

Gly Asp Leu Tyr Ile Leu Ala Gln Asn Phe Phe Tyr Glu Lys Ile Tyr
            340                 345                 350

Pro Lys Ser Asn
            355

<210> SEQ ID NO 2
<211> LENGTH: 307
<212> TYPE: PRT
<213> ORGANISM: Homo sapiens

<400> SEQUENCE: 2

Met Ala Ala Leu Leu Leu Gly Ala Val Leu Leu Val Ala Gln Pro Gln
1               5                   10                  15

Leu Val Pro Ser Arg Pro Ala Glu Leu Gly Gln Gln Glu Leu Leu Arg
                20                  25                  30

Lys Ala Gly Thr Leu Gln Asp Asp Val Arg Asp Gly Val Ala Pro Asn
            35                  40                  45

Gly Ser Ala Gln Gln Leu Pro Gln Thr Ile Ile Ile Gly Val Arg Lys
        50                  55                  60

Gly Gly Thr Arg Ala Leu Leu Glu Met Leu Ser Leu His Pro Asp Val
65                  70                  75                  80

Ala Ala Ala Glu Asn Glu Val His Phe Phe Asp Trp Glu Glu His Tyr
                85                  90                  95

Ser His Gly Leu Gly Trp Tyr Leu Ser Gln Met Pro Phe Ser Trp Pro
            100                 105                 110

His Gln Leu Thr Val Glu Lys Thr Pro Ala Tyr Phe Thr Ser Pro Lys
            115                 120                 125

Val Pro Glu Arg Val Tyr Ser Met Asn Pro Ser Ile Arg Leu Leu Leu
        130                 135                 140

Ile Leu Arg Asp Pro Ser Glu Arg Val Leu Ser Asp Tyr Thr Gln Val
145                 150                 155                 160

Phe Tyr Asn His Met Gln Lys His Lys Pro Tyr Pro Ser Ile Glu Glu
                165                 170                 175

Phe Leu Val Arg Asp Gly Arg Leu Asn Val Asp Tyr Lys Ala Leu Asn
            180                 185                 190

Arg Ser Leu Tyr His Val His Met Gln Asn Trp Leu Arg Phe Phe Pro
        195                 200                 205

Leu Arg His Ile His Ile Val Asp Gly Asp Arg Leu Ile Arg Asp Pro
210                 215                 220

Phe Pro Glu Ile Gln Lys Val Glu Arg Phe Leu Lys Leu Ser Pro Gln
225                 230                 235                 240

Ile Asn Ala Ser Asn Phe Tyr Phe Asn Lys Thr Lys Gly Phe Tyr Cys
                245                 250                 255

Leu Arg Asp Ser Gly Arg Asp Arg Cys Leu His Glu Ser Lys Gly Arg
```

```
            260                 265                 270
Ala His Pro Gln Val Asp Pro Lys Leu Leu Asn Lys Leu His Glu Tyr
                275                 280                 285

Phe His Glu Pro Asn Lys Lys Phe Glu Leu Val Gly Arg Thr Phe
    290                 295                 300

Asp Trp His
305

<210> SEQ ID NO 3
<211> LENGTH: 406
<212> TYPE: PRT
<213> ORGANISM: Homo sapiens

<400> SEQUENCE: 3

Met Ala Pro Pro Gly Pro Ala Ser Ala Leu Ser Thr Ser Ala Glu Pro
1               5                   10                  15

Leu Ser Arg Ser Ile Phe Arg Lys Phe Leu Leu Met Leu Cys Ser Leu
                20                  25                  30

Leu Thr Ser Leu Tyr Val Phe Tyr Cys Leu Ala Glu Arg Cys Gln Thr
            35                  40                  45

Leu Ser Gly Pro Val Val Gly Leu Ser Gly Gly Glu Glu Ala Gly
50                  55                  60

Ala Pro Gly Gly Gly Val Leu Ala Gly Pro Arg Glu Leu Ala Val
65                  70                  75                  80

Trp Pro Ala Ala Ala Gln Arg Lys Arg Leu Leu Gln Leu Pro Gln Trp
                85                  90                  95

Arg Arg Arg Arg Pro Pro Ala Pro Arg Asp Asp Gly Glu Glu Ala Ala
                100                 105                 110

Trp Glu Glu Glu Ser Pro Gly Leu Ser Gly Gly Pro Gly Gly Ser Gly
            115                 120                 125

Ala Gly Ser Thr Val Ala Glu Ala Pro Pro Gly Thr Leu Ala Leu Leu
        130                 135                 140

Leu Asp Glu Gly Ser Lys Gln Leu Pro Gln Ala Ile Ile Ile Gly Val
145                 150                 155                 160

Lys Lys Gly Gly Thr Arg Ala Leu Leu Glu Phe Leu Arg Val His Pro
                165                 170                 175

Asp Val Arg Ala Val Gly Ala Glu Pro His Phe Phe Asp Arg Ser Tyr
            180                 185                 190

Asp Lys Gly Leu Ala Trp Tyr Arg Asp Leu Met Pro Arg Thr Leu Asp
        195                 200                 205

Gly Gln Ile Thr Met Glu Lys Thr Pro Ser Tyr Phe Val Thr Arg Glu
    210                 215                 220

Ala Pro Ala Arg Ile Ser Ala Met Ser Lys Asp Thr Lys Leu Ile Val
225                 230                 235                 240

Val Val Arg Asp Pro Val Thr Arg Ala Ile Ser Asp Tyr Thr Gln Thr
                245                 250                 255

Leu Ser Lys Arg Pro Asp Ile Pro Thr Phe Glu Ser Leu Thr Phe Lys
            260                 265                 270

Asn Arg Thr Ala Gly Leu Ile Asp Thr Ser Trp Ser Ala Ile Gln Ile
        275                 280                 285

Gly Ile Tyr Ala Lys His Leu Glu His Trp Leu Arg His Phe Pro Ile
    290                 295                 300

Arg Gln Met Leu Phe Val Ser Gly Glu Arg Leu Ile Ser Asp Pro Ala
305                 310                 315                 320
```

```
Gly Glu Leu Gly Arg Val Gln Asp Phe Leu Gly Lys Arg Ile Ile
                325                 330                 335

Thr Asp Lys His Phe Tyr Phe Asn Lys Thr Lys Gly Phe Pro Cys Leu
            340                 345                 350

Lys Lys Ala Glu Gly Ser Ser Arg Pro His Cys Leu Gly Lys Thr Lys
        355                 360                 365

Gly Arg Thr His Pro Glu Ile Asp Arg Glu Val Val Arg Arg Leu Arg
    370                 375                 380

Glu Phe Tyr Arg Pro Phe Asn Leu Lys Phe Tyr Gln Met Thr Gly His
385                 390                 395                 400

Asp Phe Gly Trp Asp Gly
                405

<210> SEQ ID NO 4
<211> LENGTH: 390
<212> TYPE: PRT
<213> ORGANISM: Homo sapiens

<400> SEQUENCE: 4

Met Gly Gln Arg Leu Ser Gly Gly Arg Ser Cys Leu Asp Val Pro Gly
1               5                   10                  15

Arg Leu Leu Pro Gln Pro Pro Pro Pro Pro Val Arg Arg Lys
                20                  25                  30

Leu Ala Leu Leu Phe Ala Met Leu Cys Val Trp Leu Tyr Met Phe Leu
            35                  40                  45

Tyr Ser Cys Ala Gly Ser Cys Ala Ala Pro Gly Leu Leu Leu Leu
        50                  55                  60

Gly Ser Gly Ser Arg Ala Ala His Asp Pro Pro Ala Leu Ala Thr Ala
65                  70                  75                  80

Pro Asp Gly Thr Pro Pro Arg Leu Pro Phe Arg Ala Pro Pro Ala Thr
                85                  90                  95

Pro Leu Ala Ser Gly Lys Glu Met Ala Glu Gly Ala Ala Ser Pro Glu
            100                 105                 110

Glu Gln Ser Pro Glu Val Pro Asp Ser Pro Ser Pro Ile Ser Ser Phe
        115                 120                 125

Phe Ser Gly Ser Gly Ser Lys Gln Leu Pro Gln Ala Ile Ile Ile Gly
    130                 135                 140

Val Lys Lys Gly Gly Thr Arg Ala Leu Leu Glu Phe Leu Arg Val His
145                 150                 155                 160

Pro Asp Val Arg Ala Val Gly Ala Glu Pro His Phe Phe Asp Arg Ser
                165                 170                 175

Tyr Asp Lys Gly Leu Ala Trp Tyr Arg Asp Leu Met Pro Arg Thr Leu
            180                 185                 190

Asp Gly Gln Ile Thr Met Glu Lys Thr Pro Ser Tyr Phe Val Thr Arg
        195                 200                 205

Glu Ala Pro Ala Arg Ile Ser Ala Met Ser Lys Asp Thr Lys Leu Ile
    210                 215                 220

Val Val Val Arg Asp Pro Val Thr Arg Ala Ile Ser Asp Tyr Thr Gln
225                 230                 235                 240

Thr Leu Ser Lys Arg Pro Asp Ile Pro Thr Phe Glu Ser Leu Thr Phe
                245                 250                 255

Lys Asn Arg Thr Ala Gly Leu Ile Asp Thr Ser Trp Ser Ala Ile Gln
            260                 265                 270

Ile Gly Ile Tyr Ala Lys His Leu Glu His Trp Leu Arg His Phe Pro
        275                 280                 285
```

```
Ile Arg Gln Met Leu Phe Val Ser Gly Glu Arg Leu Ile Ser Asp Pro
        290                 295                 300

Ala Gly Glu Leu Gly Arg Val Gln Asp Phe Leu Gly Leu Lys Arg Ile
305                 310                 315                 320

Ile Thr Asp Lys His Phe Tyr Phe Asn Lys Thr Lys Gly Phe Pro Cys
                    325                 330                 335

Leu Lys Lys Ala Glu Gly Ser Ser Arg Pro His Cys Leu Gly Lys Thr
                340                 345                 350

Lys Gly Arg Thr His Pro Glu Ile Asp Arg Glu Val Val Arg Arg Leu
            355                 360                 365

Arg Glu Phe Tyr Arg Pro Phe Asn Leu Lys Phe Tyr Gln Met Thr Gly
370                 375                 380

His Asp Phe Gly Trp Asp
385                 390

<210> SEQ ID NO 5
<211> LENGTH: 401
<212> TYPE: PRT
<213> ORGANISM: Mus musculus

<400> SEQUENCE: 5

Met Val Glu Arg Ala Ser Lys Phe Val Leu Val Val Ala Gly Ser Ala
1               5                   10                  15

Cys Phe Met Leu Ile Leu Tyr Gln Tyr Ala Gly Pro Gly Leu Ser Leu
                20                  25                  30

Gly Ala Pro Gly Gly Arg Val Pro Pro Asp Asp Leu Asp Leu Phe Pro
            35                  40                  45

Thr Pro Asp Pro His Tyr Glu Lys Lys Tyr Tyr Phe Pro Val Arg Glu
        50                  55                  60

Leu Glu Arg Ser Leu Arg Phe Asp Met Lys Gly Asp Asp Val Ile Val
65                  70                  75                  80

Phe Leu His Ile Gln Lys Thr Gly Gly Thr Thr Phe Gly Arg His Leu
                85                  90                  95

Val Gln Asn Val Arg Leu Glu Val Pro Cys Asp Cys Arg Pro Gly Gln
                100                 105                 110

Lys Lys Cys Thr Cys Tyr Arg Pro Asn Arg Arg Glu Thr Trp Leu Phe
            115                 120                 125

Ser Arg Phe Ser Thr Gly Trp Ser Cys Gly Leu His Ala Asp Trp Thr
130                 135                 140

Glu Leu Thr Asn Cys Val Pro Gly Val Leu Asp Arg Arg Asp Pro Ala
145                 150                 155                 160

Gly Leu Arg Ser Pro Arg Lys Phe Tyr Tyr Ile Thr Leu Leu Arg Asp
                165                 170                 175

Pro Val Ser Arg Tyr Leu Ser Glu Trp Arg His Val Gln Arg Gly Ala
            180                 185                 190

Thr Trp Lys Thr Ser Leu His Met Cys Asp Gly Arg Thr Pro Thr Pro
        195                 200                 205

Glu Glu Leu Pro Pro Cys Tyr Glu Gly Thr Asp Trp Ser Gly Cys Thr
210                 215                 220

Leu Gln Glu Phe Met Asp Cys Pro Tyr Asn Leu Ala Asn Asn Arg Gln
225                 230                 235                 240

Val Arg Met Leu Ala Asp Leu Ser Leu Val Gly Cys Tyr Asn Leu Ser
                245                 250                 255

Phe Ile Pro Glu Ser Lys Arg Ala Gln Leu Leu Leu Glu Ser Ala Lys
```

```
                    260                 265                 270
Lys Asn Leu Arg Gly Met Ala Phe Phe Gly Leu Thr Glu Phe Gln Arg
            275                 280                 285

Lys Thr Gln Tyr Leu Phe Glu Arg Thr Phe Asn Leu Lys Phe Ile Arg
        290                 295                 300

Pro Phe Met Gln Tyr Asn Ser Thr Arg Ala Gly Gly Val Glu Val Asp
305                 310                 315                 320

Glu Asp Thr Ile Arg His Ile Glu Glu Leu Asn Asp Leu Asp Met Gln
                    325                 330                 335

Leu Tyr Asp Tyr Ala Lys Asp Leu Phe Gln Gln Arg Tyr Gln Tyr Lys
            340                 345                 350

Arg Gln Leu Glu Arg Glu Gln Arg Leu Arg Asn Arg Glu Glu Arg
        355                 360                 365

Leu Leu His Arg Ser Lys Glu Ala Leu Pro Arg Glu Asp Pro Glu Glu
            370                 375                 380

Pro Gly Arg Val Pro Thr Glu Asp Tyr Met Ser His Ile Ile Glu Lys
385                 390                 395                 400

Trp

<210> SEQ ID NO 6
<211> LENGTH: 506
<212> TYPE: PRT
<213> ORGANISM: Mus musculus

<400> SEQUENCE: 6

Met Asp Glu Lys Ser Asn Lys Leu Leu Ala Leu Val Met Leu Phe
1               5                   10                  15

Leu Phe Ala Val Ile Val Leu Gln Tyr Val Cys Pro Gly Thr Glu Cys
                20                  25                  30

Gln Leu Leu Arg Leu Gln Ala Phe Ser Ser Pro Val Pro Asp Pro Tyr
            35                  40                  45

Arg Ser Glu Asp Glu Ser Ser Ala Arg Phe Val Pro Arg Tyr Asn Phe
    50                  55                  60

Ser Arg Gly Asp Leu Leu Arg Lys Val Asp Phe Asp Ile Lys Gly Asp
65                  70                  75                  80

Asp Leu Ile Val Phe Leu His Ile Gln Lys Thr Gly Gly Thr Thr Phe
                85                  90                  95

Gly Arg His Leu Val Arg Asn Ile Gln Leu Glu Gln Pro Cys Glu Cys
            100                 105                 110

Arg Val Gly Gln Lys Lys Cys Thr Cys His Arg Pro Gly Lys Arg Glu
        115                 120                 125

Thr Trp Leu Phe Ser Arg Phe Ser Thr Gly Trp Ser Cys Gly Leu His
    130                 135                 140

Ala Asp Trp Thr Glu Leu Thr Ser Cys Val Pro Ala Val Val Asp Gly
145                 150                 155                 160

Lys Arg Asp Ala Arg Leu Arg Pro Ser Arg Trp Arg Ile Phe Gln Ile
                165                 170                 175

Leu Asp Gly Thr Ser Lys Asp Arg Trp Gly Ser Ser Asn Phe Asn Ser
            180                 185                 190

Gly Ala Asn Ser Pro Ser Ser Thr Lys Pro Arg Ser Thr Ser Lys Ser
        195                 200                 205

Gly Lys Asn Phe His Tyr Ile Thr Ile Leu Arg Asp Pro Val Ser Arg
    210                 215                 220

Tyr Leu Ser Glu Trp Arg His Val Gln Arg Gly Ala Thr Trp Lys Ala
```

```
                225                 230                 235                 240
Ser Leu His Val Cys Asp Gly Arg Pro Pro Thr Ser Glu Glu Leu Pro
                    245                 250                 255

Ser Cys Tyr Thr Gly Asp Asp Trp Ser Gly Cys Pro Leu Lys Glu Phe
                    260                 265                 270

Met Asp Cys Pro Tyr Asn Leu Ala Asn Asn Arg Gln Val Arg Met Leu
                    275                 280                 285

Ser Asp Leu Thr Leu Val Gly Cys Tyr Asn Leu Ser Val Met Pro Glu
                290                 295                 300

Lys Gln Arg Asn Lys Val Leu Leu Glu Ser Ala Lys Ser Asn Leu Lys
305                 310                 315                 320

His Met Ala Phe Phe Gly Leu Thr Glu Phe Gln Arg Lys Thr Gln Tyr
                    325                 330                 335

Leu Phe Glu Lys Thr Phe Asn Met Asn Phe Ile Ser Pro Phe Thr Gln
                    340                 345                 350

Tyr Asn Thr Thr Arg Ala Ser Ser Val Glu Ile Asn Glu Glu Ile Gln
                    355                 360                 365

Lys Arg Ile Glu Gly Leu Asn Phe Leu Asp Met Glu Leu Tyr Ser Tyr
                370                 375                 380

Ala Lys Asp Leu Phe Leu Gln Arg Tyr Gln Phe Met Arg Gln Lys Glu
385                 390                 395                 400

His Gln Asp Ala Arg Arg Lys Arg Gln Glu Gln Arg Lys Phe Leu Lys
                    405                 410                 415

Gly Arg Phe Leu Gln Thr His Phe Gln Ser Gln Ser Gln Gly Gln Ser
                    420                 425                 430

Gln Ser Gln Ser Pro Gly Gln Asn Leu Ser Gln Asn Pro Asn Pro Asn
                435                 440                 445

Pro Asn Gln Asn Leu Thr Gln Asn Leu Ser His Asn Leu Thr Pro Ser
                    450                 455                 460

Ser Asn Pro Asn Ser Thr Gln Arg Glu Asn Arg Gly Ser Gln Lys Gln
465                 470                 475                 480

Gly Ser Gly Gln Gly Gln Gly Asp Ser Gly Thr Ser Asn Gly Thr Asn
                    485                 490                 495

Asp Tyr Ile Gly Ser Val Glu Thr Trp Arg
                    500                 505

<210> SEQ ID NO 7
<211> LENGTH: 470
<212> TYPE: PRT
<213> ORGANISM: Mus musculus

<400> SEQUENCE: 7

Met Asp Glu Arg Phe Asn Lys Trp Leu Leu Thr Pro Val Leu Thr Phe
1               5                   10                  15

Leu Phe Val Val Ile Met Tyr Gln Tyr Val Ser Pro Ser Cys Thr Ser
                    20                  25                  30

Ser Cys Thr Asn Phe Gly Glu Gln Leu Arg Ser Gly Glu Ala Arg Pro
                    35                  40                  45

Pro Ala Val Pro Ser Pro Ala Arg Arg Ala Gln Ala Pro Leu Asp Glu
                50                  55                  60

Trp Glu Arg Arg Pro Gln Leu Pro Pro Pro Arg Gly Pro Pro Glu
65                  70                  75                  80

Gly Ser Arg Gly Val Ala Ala Pro Glu Asp Glu Asp Glu Asp Pro Gly
                    85                  90                  95
```

-continued

Asp Pro Glu Glu Glu Glu Glu Glu Glu Pro Asp Pro Glu
         100                 105                 110

Ala Pro Glu Asn Gly Ser Leu Pro Arg Phe Val Pro Arg Phe Asn Phe
             115                 120                 125

Thr Leu Lys Asp Leu Thr Arg Phe Val Asp Phe Asn Ile Lys Gly Arg
        130                 135                 140

Asp Val Ile Val Phe Leu His Ile Gln Lys Thr Gly Gly Thr Thr Phe
145                 150                 155                 160

Gly Arg His Leu Val Lys Asn Ile Arg Leu Glu Gln Pro Cys Ser Cys
                165                 170                 175

Lys Ala Gly Gln Lys Lys Cys Thr Cys His Arg Pro Gly Lys Lys Glu
            180                 185                 190

Thr Trp Leu Phe Ser Arg Phe Ser Thr Gly Trp Ser Cys Gly Leu His
        195                 200                 205

Ala Asp Trp Thr Glu Leu Thr Asn Cys Val Pro Ala Ile Met Glu Lys
210                 215                 220

Lys Asp Cys Pro Arg Asn His Ser His Thr Arg Asn Phe Tyr Tyr Ile
225                 230                 235                 240

Thr Met Leu Arg Asp Pro Val Ser Arg Tyr Leu Ser Glu Trp Lys His
                245                 250                 255

Val Gln Arg Gly Ala Thr Trp Lys Thr Ser Leu His Met Cys Asp Gly
            260                 265                 270

Arg Ser Pro Thr Pro Asp Glu Leu Pro Thr Cys Tyr Pro Gly Asp Asp
        275                 280                 285

Trp Ser Gly Val Ser Leu Arg Glu Phe Met Asp Cys Ser Tyr Asn Leu
290                 295                 300

Ala Asn Asn Arg Gln Val Arg Met Leu Ala Asp Leu Ser Leu Val Gly
305                 310                 315                 320

Cys Tyr Asn Leu Thr Phe Met Asn Glu Ser Glu Arg Asn Thr Ile Leu
                325                 330                 335

Leu Gln Ser Ala Lys Asn Asn Leu Lys Asn Met Ala Phe Phe Gly Leu
            340                 345                 350

Thr Glu Phe Gln Arg Lys Thr Gln Phe Leu Phe Glu Arg Thr Phe Asn
        355                 360                 365

Leu Lys Phe Ile Ser Pro Phe Thr Gln Phe Asn Ile Thr Arg Ala Ser
370                 375                 380

Asn Val Asp Ile Asn Asp Gly Ala Arg Gln His Ile Glu Glu Leu Asn
385                 390                 395                 400

Phe Leu Asp Met Gln Leu Tyr Glu Tyr Ala Lys Asp Leu Phe Gln Gln
                405                 410                 415

Arg Tyr His His Thr Lys Gln Leu Glu His Gln Arg Asp Arg Gln Lys
            420                 425                 430

Arg Arg Glu Glu Arg Arg Leu Gln Arg Glu His Arg Ala His Arg Trp
        435                 440                 445

Pro Lys Glu Asp Arg Ala Met Glu Gly Thr Val Thr Glu Asp Tyr Asn
        450                 455                 460

Ser Gln Val Val Arg Trp
465                 470

<210> SEQ ID NO 8
<211> LENGTH: 291
<212> TYPE: PRT
<213> ORGANISM: Rattus norvegicus

<400> SEQUENCE: 8

```
Met Glu Phe Ser Arg Pro Pro Leu Val His Val Lys Gly Ile Pro Leu
1               5                   10                  15

Ile Lys Tyr Phe Ala Glu Thr Ile Gly Pro Leu Gln Asn Phe Thr Ala
                20                  25                  30

Trp Pro Asp Asp Leu Leu Ile Ser Thr Tyr Pro Lys Ser Gly Thr Thr
            35                  40                  45

Trp Met Ser Glu Ile Leu Asp Met Ile Tyr Gln Gly Gly Lys Leu Glu
        50                  55                  60

Lys Cys Gly Arg Ala Pro Ile Tyr Ala Arg Val Pro Phe Leu Glu Phe
65                  70                  75                  80

Lys Cys Pro Gly Val Pro Ser Gly Leu Glu Thr Leu Glu Glu Thr Pro
                85                  90                  95

Ala Pro Arg Leu Leu Lys Thr His Leu Pro Leu Ser Leu Leu Pro Gln
            100                 105                 110

Ser Leu Leu Asp Gln Lys Val Lys Val Ile Tyr Ile Ala Arg Asn Ala
        115                 120                 125

Lys Asp Val Val Ser Tyr Tyr Asn Phe Tyr Asn Met Ala Lys Leu
    130                 135                 140

His Pro Asp Pro Gly Thr Trp Asp Ser Phe Leu Glu Asn Phe Met Asp
145                 150                 155                 160

Gly Glu Val Ser Tyr Gly Ser Trp Tyr Gln His Val Lys Glu Trp Trp
                165                 170                 175

Glu Leu Arg His Thr His Pro Val Leu Tyr Leu Phe Tyr Glu Asp Ile
            180                 185                 190

Lys Glu Asn Pro Lys Arg Glu Ile Lys Ile Leu Glu Phe Leu Gly
    195                 200                 205

Arg Ser Leu Pro Glu Glu Thr Val Asp Ser Ile Val His His Thr Ser
    210                 215                 220

Phe Lys Lys Met Lys Glu Asn Cys Met Thr Asn Tyr Thr Thr Ile Pro
225                 230                 235                 240

Thr Glu Ile Met Asp His Asn Val Ser Pro Phe Met Arg Lys Gly Thr
            245                 250                 255

Thr Gly Asp Trp Lys Asn Thr Phe Thr Val Ala Gln Asn Glu Arg Phe
        260                 265                 270

Asp Ala His Tyr Ala Lys Thr Met Thr Asp Cys Asp Phe Lys Phe Arg
        275                 280                 285

Cys Glu Leu
    290
```